United States Patent
Burrell et al.

(10) Patent No.: US 8,608,642 B2
(45) Date of Patent: Dec. 17, 2013

(54) METHODS AND DEVICES FOR TREATING MORBID OBESITY USING HYDROGEL

(75) Inventors: Janna M. Burrell, Cincinnati, OH (US); Randal T. Byrum, South Lebanon, OH (US); Robert Louis Koch, Jr., Cincinnati, OH (US); Larry D. Pool, Mason, OH (US); Christopher W. Widenhouse, Clarksville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 430 days.

(21) Appl. No.: 12/712,466

(22) Filed: Feb. 25, 2010

(65) Prior Publication Data
US 2011/0207994 A1 Aug. 25, 2011

(51) Int. Cl.
*A61F 2/00* (2006.01)
*A61F 13/00* (2006.01)

(52) U.S. Cl.
USPC ............... 600/37; 600/30; 606/151; 606/155; 606/156; 606/158; 606/191; 606/192; 606/193; 606/194; 606/195; 604/38; 604/121; 604/135; 604/141; 604/143; 604/152; 604/153; 604/140; 604/891.1; 604/890.1; 604/892.1; 604/31; 604/503; 604/504; 604/505; 604/65; 604/66; 604/67; 128/898

(58) Field of Classification Search
USPC ......... 606/151, 155, 156, 158, 191–195, 153; 600/30, 37; 604/38, 121, 135, 141, 604/143, 152, 140, 891.1, 890.1, 892.1, 31, 604/503–505, 65–67; 128/898
See application file for complete search history.

(56) References Cited

U.S. PATENT DOCUMENTS

| | | | |
|---|---|---|---|
| 4,311,146 | A | 1/1982 | Wonder |
| 4,315,509 | A | 2/1982 | Smit |
| 4,723,547 | A | 2/1988 | Kullas et al. |

(Continued)

FOREIGN PATENT DOCUMENTS

| | | |
|---|---|---|
| EP | 0315222 B1 | 5/1989 |
| EP | 0648510 B1 | 4/1995 |

(Continued)

OTHER PUBLICATIONS

Byrne, M.E. et al., "Molecular Imprinting within Hydrogels," Adv. Drug Deliv. Revs., vol. 54 (2002) pp. 149-161.

(Continued)

*Primary Examiner* — Christine Matthews
*Assistant Examiner* — Sunita Reddy
(74) *Attorney, Agent, or Firm* — Frost Brown Todd LLC

(57) ABSTRACT

An environmentally sensitive hydrogel material swells or collapses in response to a parameter such as pH level associated with consumption of food by a patient. This swelling or collapsing is harnessed to treat morbid obesity or some other condition of the patient. The swelling or collapsing of the hydrogel may be used to tighten a gastric band or gastric valve when the patient starts eating; then loosen the band or valve when the patient is between meals. The swelling or collapsing of the hydrogel may also be used to increase the size of a space occupying device in the patient's stomach when the patient starts eating; then decrease the size of the space occupying device when the patient is between meals. The swelling or collapsing of the hydrogel may also be used to selectively restrict the absorption of nutrients within a patient's gastrointestinal tract, such as in the duodenum.

14 Claims, 11 Drawing Sheets

(56) References Cited

U.S. PATENT DOCUMENTS

| | | |
|---|---|---|
| 4,735,616 A | 4/1988 | Eibl et al. |
| 4,766,898 A | 8/1988 | Hardy et al. |
| 4,874,368 A | 10/1989 | Miller et al. |
| 4,899,747 A | 2/1990 | Garren et al. |
| 5,004,469 A | 4/1991 | Palmieri et al. |
| 5,154,320 A | 10/1992 | Bolduc |
| 5,234,454 A | 8/1993 | Bangs |
| 5,254,113 A | 10/1993 | Wilk |
| 5,312,333 A | 5/1994 | Churinetz et al. |
| 5,324,305 A | 6/1994 | Kanner |
| 5,372,585 A | 12/1994 | Tiefenbrun et al. |
| 5,443,481 A | 8/1995 | Lee |
| 5,474,540 A | 12/1995 | Miller et al. |
| 5,529,577 A | 6/1996 | Hammerslag |
| 5,582,596 A | 12/1996 | Fukunaga et al. |
| 5,605,541 A | 2/1997 | Holm |
| 5,718,711 A | 2/1998 | Berenstein et al. |
| 5,752,965 A | 5/1998 | Francis et al. |
| 5,759,169 A | 6/1998 | Marx |
| 5,759,171 A | 6/1998 | Coelho et al. |
| 5,779,672 A | 7/1998 | Dorandy, Jr. |
| 5,814,022 A | 9/1998 | Antanavich et al. |
| 5,844,087 A | 12/1998 | Zimmerman et al. |
| 5,895,412 A | 4/1999 | Tucker |
| 5,928,611 A | 7/1999 | Leung |
| 5,980,508 A * | 11/1999 | Cardamone et al. ....... 604/890.1 |
| 5,981,621 A | 11/1999 | Clark et al. |
| 6,007,515 A | 12/1999 | Epstein et al. |
| 6,010,714 A | 1/2000 | Leung et al. |
| 6,055,828 A | 5/2000 | Rivera et al. |
| 6,099,807 A | 8/2000 | Leung |
| 6,113,571 A | 9/2000 | Zinger et al. |
| 6,143,352 A | 11/2000 | Clark et al. |
| 6,143,805 A | 11/2000 | Hickey et al. |
| 6,162,239 A | 12/2000 | Manhes |
| 6,174,919 B1 | 1/2001 | Hickey |
| 6,183,593 B1 | 2/2001 | Narang et al. |
| 6,206,905 B1 | 3/2001 | Holm et al. |
| 6,217,603 B1 | 4/2001 | Clark et al. |
| 6,228,051 B1 | 5/2001 | Trumbull |
| 6,234,994 B1 | 5/2001 | Zinger |
| 6,245,933 B1 | 6/2001 | Malofsky et al. |
| 6,280,399 B1 | 8/2001 | Rossin et al. |
| 6,283,933 B1 | 9/2001 | D'Alessio et al. |
| 6,302,898 B1 | 10/2001 | Edwards et al. |
| 6,306,243 B1 | 10/2001 | Clark et al. |
| 6,310,166 B1 | 10/2001 | Hickey et al. |
| 6,322,852 B1 | 11/2001 | Leung |
| 6,325,810 B1 | 12/2001 | Hamilton et al. |
| 6,340,097 B1 | 1/2002 | D'Alessio et al. |
| 6,352,704 B1 | 3/2002 | Nicholson et al. |
| 6,372,313 B1 | 4/2002 | D'Alessio et al. |
| 6,376,019 B1 | 4/2002 | Leung |
| 6,394,975 B1 | 5/2002 | Epstein |
| 6,394,982 B1 | 5/2002 | Ehrenfels |
| 6,398,797 B2 | 6/2002 | Bombard et al. |
| 6,412,639 B1 | 7/2002 | Hickey |
| 6,420,590 B1 | 7/2002 | Badejo et al. |
| 6,425,704 B2 | 7/2002 | Voiers et al. |
| 6,428,233 B1 | 8/2002 | Clark et al. |
| 6,428,234 B1 | 8/2002 | Bobo et al. |
| 6,432,084 B1 | 8/2002 | Levinson et al. |
| 6,433,096 B1 | 8/2002 | Hickey et al. |
| 6,439,789 B1 | 8/2002 | Balance et al. |
| 6,454,739 B1 | 9/2002 | Chang |
| 6,454,785 B2 | 9/2002 | De Hoyes Garza |
| 6,455,064 B1 | 9/2002 | Narang et al. |
| 6,458,095 B1 | 10/2002 | Wirt et al. |
| 6,461,292 B1 | 10/2002 | Forsell |
| 6,461,361 B1 | 10/2002 | Epstein |
| 6,461,367 B1 | 10/2002 | Kirsch et al. |
| 6,464,663 B1 | 10/2002 | Zinger |
| 6,468,520 B1 | 10/2002 | Rowe et al. |
| 6,470,892 B1 | 10/2002 | Forsell |
| 6,471,670 B1 | 10/2002 | Enrenfels et al. |
| 6,478,191 B1 | 11/2002 | D'Alessio et al. |
| 6,488,197 B1 | 12/2002 | Whitman |
| 6,488,650 B1 | 12/2002 | Epstein et al. |
| 6,488,944 B2 | 12/2002 | Narang |
| 6,491,201 B1 | 12/2002 | Whitman |
| 6,494,896 B1 | 12/2002 | D'Alessio et al. |
| 6,512,023 B1 | 1/2003 | Malofsky et al. |
| 6,527,749 B1 | 3/2003 | Roby et al. |
| 6,540,716 B1 | 4/2003 | Holm |
| 6,547,467 B2 | 4/2003 | Quintero |
| 6,565,840 B1 | 5/2003 | Clark et al. |
| 6,579,469 B1 | 6/2003 | Nicholson et al. |
| 6,585,967 B2 | 7/2003 | Narang et al. |
| 6,589,269 B2 | 7/2003 | Zhu et al. |
| 6,592,281 B2 | 7/2003 | Clark et al. |
| 6,595,940 B1 | 7/2003 | D'Alessio et al. |
| 6,599,304 B1 | 7/2003 | Selmon et al. |
| 6,602,496 B2 | 8/2003 | Hedgpeth et al. |
| 6,605,667 B1 | 8/2003 | Badejo et al. |
| 6,607,631 B1 | 8/2003 | Badejo et al. |
| 6,613,020 B1 | 9/2003 | Holm et al. |
| 6,616,019 B2 | 9/2003 | D'Alessio et al. |
| 6,620,846 B1 | 9/2003 | Jonn et al. |
| 6,637,967 B2 | 10/2003 | Bobo et al. |
| 6,666,873 B1 | 12/2003 | Cassell |
| 6,676,322 B1 | 1/2004 | Leung |
| 6,681,979 B2 | 1/2004 | Whitman |
| 6,695,199 B2 | 2/2004 | Whitman |
| 6,705,790 B2 | 3/2004 | Quintero et al. |
| 6,743,858 B2 | 6/2004 | Hickey et al. |
| 6,746,667 B2 | 6/2004 | Badejo et al. |
| 6,748,950 B2 | 6/2004 | Clark et al. |
| 6,755,869 B2 | 6/2004 | Geitz |
| 6,764,467 B1 | 7/2004 | Roby et al. |
| 6,767,552 B2 | 7/2004 | Narang |
| 6,779,657 B2 | 8/2004 | Mainwaring et al. |
| 6,783,514 B2 | 8/2004 | Tovey et al. |
| 6,802,416 B1 | 10/2004 | D'Alessio et al. |
| 6,802,822 B1 | 10/2004 | Dodge |
| 6,811,341 B2 | 11/2004 | Crane |
| D500,085 S | 12/2004 | Cotter et al. |
| 6,837,027 B2 | 1/2005 | Hickey |
| 6,863,660 B2 | 3/2005 | Marx |
| 6,884,232 B2 | 4/2005 | Hagmann et al. |
| 6,896,684 B2 | 5/2005 | Monassevitch et al. |
| 6,896,838 B2 | 5/2005 | D'Alessio |
| 6,921,381 B2 | 7/2005 | Spero et al. |
| 6,942,875 B2 | 9/2005 | Hedgpeth |
| 6,960,040 B2 | 11/2005 | D'Alessio et al. |
| 6,997,941 B2 | 2/2006 | Sharkey et al. |
| 7,008,442 B2 | 3/2006 | Brightbill |
| 7,025,753 B2 | 4/2006 | Reever |
| 7,025,776 B1 | 4/2006 | Houser et al. |
| 7,033,373 B2 | 4/2006 | de la Torre et al. |
| 7,037,344 B2 | 5/2006 | Kagan et al. |
| 7,128,241 B2 | 10/2006 | Leung |
| 7,138,135 B2 | 11/2006 | Chen et al. |
| 7,217,254 B2 | 5/2007 | Kirwan et al. |
| 7,238,195 B2 | 7/2007 | Viola |
| 7,306,390 B2 | 12/2007 | Quintero et al. |
| 7,331,463 B2 | 2/2008 | Hickey |
| 7,338,511 B2 | 3/2008 | Mirigian et al. |
| 7,351,240 B2 | 4/2008 | Hassler, Jr. et al. |
| 7,371,345 B2 | 5/2008 | Stewart et al. |
| 7,390,294 B2 | 6/2008 | Hassler, Jr. |
| 7,416,528 B2 | 8/2008 | Crawford et al. |
| 7,431,730 B2 | 10/2008 | Viola |
| 7,442,165 B2 | 10/2008 | Forsell |
| 7,470,251 B2 | 12/2008 | Shah |
| 7,517,356 B2 | 4/2009 | Heinrich |
| 7,621,863 B2 | 11/2009 | Forsell |
| 2002/0037310 A1 | 3/2002 | Jonn et al. |
| 2002/0048480 A1 | 4/2002 | D'Alessio et al. |
| 2002/0055573 A1 | 5/2002 | Malofsky et al. |
| 2002/0119184 A1 | 8/2002 | Nicholson et al. |
| 2002/0147462 A1 | 10/2002 | Mair et al. |
| 2002/0165483 A1 | 11/2002 | Miller et al. |
| 2002/0173770 A1 | 11/2002 | Flory et al. |
| 2003/0031499 A1 | 2/2003 | Heard et al. |

(56) References Cited

U.S. PATENT DOCUMENTS

| | | |
|---|---|---|
| 2003/0032833 A1 | 2/2003 | Badejo et al. |
| 2003/0039781 A1 | 2/2003 | D'Alessio et al. |
| 2003/0060380 A1 | 3/2003 | Ayarza et al. |
| 2003/0080151 A1 | 5/2003 | D'Alessio et al. |
| 2003/0082116 A1 | 5/2003 | Badejo et al. |
| 2003/0149128 A1 | 8/2003 | Malofsky et al. |
| 2003/0202956 A1 | 10/2003 | Clark et al. |
| 2004/0111115 A1 | 6/2004 | Maw |
| 2004/0137067 A1 | 7/2004 | Narang et al. |
| 2004/0148034 A1* | 7/2004 | Kagan et al. ............... 623/23.65 |
| 2004/0149780 A1* | 8/2004 | Poile et al. ................... 222/386 |
| 2004/0151688 A1 | 8/2004 | Sherbondy et al. |
| 2004/0190975 A1 | 9/2004 | Goodman et al. |
| 2004/0223932 A1 | 11/2004 | Hedgpeth et al. |
| 2004/0223946 A1 | 11/2004 | Kidd et al. |
| 2004/0254561 A1 | 12/2004 | Stenton |
| 2005/0033328 A1 | 2/2005 | Laufer et al. |
| 2005/0042266 A1 | 2/2005 | Narang |
| 2005/0047846 A1 | 3/2005 | Narang et al. |
| 2005/0070935 A1 | 3/2005 | Ortiz |
| 2005/0147457 A1 | 7/2005 | Badejo et al. |
| 2005/0177226 A1 | 8/2005 | Banik et al. |
| 2005/0182443 A1 | 8/2005 | Jonn et al. |
| 2005/0228446 A1 | 10/2005 | Mooradian et al. |
| 2005/0245957 A1 | 11/2005 | Starkebaum et al. |
| 2005/0256446 A1 | 11/2005 | Criscuolo et al. |
| 2005/0267406 A1* | 12/2005 | Hassler, Jr. ................. 604/96.01 |
| 2005/0283118 A1 | 12/2005 | Uth et al. |
| 2006/0009099 A1 | 1/2006 | Jonn et al. |
| 2006/0020278 A1* | 1/2006 | Burnett et al. ............... 606/153 |
| 2006/0173472 A1* | 8/2006 | Starkebaum et al. ......... 606/153 |
| 2006/0211914 A1 | 9/2006 | Hassler, Jr. et al. |
| 2006/0235448 A1 | 10/2006 | Roslin et al. |
| 2006/0247768 A1 | 11/2006 | Starkebaum |
| 2007/0100369 A1* | 5/2007 | Cragg et al. ................. 606/192 |
| 2007/0118060 A1 | 5/2007 | Gefen et al. |
| 2008/0103593 A1 | 5/2008 | Ortiz et al. |
| 2008/0154228 A1 | 6/2008 | Ortiz et al. |
| 2008/0269715 A1 | 10/2008 | Faller et al. |
| 2009/0024152 A1* | 1/2009 | Boyden et al. ............... 606/155 |
| 2009/0192535 A1* | 7/2009 | Kasic, II ...................... 606/157 |
| 2009/0259246 A1* | 10/2009 | Eskaros et al. ............... 606/192 |

FOREIGN PATENT DOCUMENTS

| | | |
|---|---|---|
| EP | 0669100 B1 | 8/1995 |
| EP | 0716833 A2 | 6/1996 |
| EP | 1073484 B1 | 2/2001 |
| EP | 1078600 A2 | 2/2001 |
| EP | 1113839 B1 | 7/2001 |
| EP | 1159081 A1 | 12/2001 |
| EP | 1381321 A2 | 1/2004 |
| EP | 1411836 B1 | 4/2004 |
| GB | 2374905 | 10/2002 |
| JP | 10262986 | 10/1998 |
| JP | 2000217830 | 8/2000 |
| JP | 2001157716 | 6/2001 |
| JP | 2001190558 | 7/2001 |
| JP | 2002233581 | 8/2002 |
| JP | 2003126268 | 5/2003 |
| JP | 2005169125 | 6/2005 |
| JP | 2005028009 | 2/2006 |
| WO | WO 92/09651 | 6/1992 |
| WO | WO 95/31137 A1 | 11/1995 |
| WO | WO 98/41154 A1 | 9/1998 |
| WO | WO 99/17833 A1 | 4/1999 |
| WO | WO 99/30629 A1 | 6/1999 |
| WO | WO 01/12257 | 2/2001 |
| WO | WO 01/24869 A1 | 4/2001 |
| WO | WO 01/62158 A2 | 8/2001 |
| WO | WO 01/62333 A1 | 8/2001 |
| WO | WO 02/067785 A2 | 9/2002 |

OTHER PUBLICATIONS

Hoffman, A.S., "Hydrogels for Biomedical Applications," Adv. Drug Deliv. Revs., vol. 54 (2002) pp. 3-12.

Jeong, B. et al., "Thermosensitive Sol-Gel Reversible Hydrogels," Ad.v Drug Deliv. Revs., vol. 54 (2002) pp. 37-51.

Miyata, T. et al., "Biomolecule-Sensitive Hydrogels," Adv. Drug Deliv. Revs., vol. 54 (2002) pp. 79-98.

Peppas, N.A., "Physiologically Responsive Gels," J. Bioact. Compat. Polym., vol. 6 (1991) pp. 241-146.

Qiu, Y. et al., "Environment-Sensitive Hydrogels for Drug Delivery," Adv. Drug Deliv. Revs., vol. 53 (2001) pp. 321-339.

International Search Report dated May 9, 2011 for Application No. PCT/US2011/024213.

Peppas, N., ed., *Hydrogels in Medicine and Pharmacy: Fundamentals*, CRC Press, 1986, Boca Raton, FL. (Bibliography only).

* cited by examiner

METHODS AND DEVICES FOR TREATING MORBID OBESITY USING HYDROGEL

BACKGROUND

A variety of systems and devices have been made and used for treating morbid obesity. Some such systems and devices include adjustable gastric band systems, which are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of gastric bands are disclosed in U.S. Pat. No. 7,416,528, entitled "Latching Device for Gastric Band," issued Aug. 26, 2008, the disclosure of which is incorporated by reference herein; and U.S. Pub. No. 2006/0211914, entitled "System and Method for Determining Implanted Device Positioning and Obtaining Pressure Data," published Sep. 21, 2006, the disclosure of which is incorporated by reference herein. Fluid may be added to the bladder by using a syringe and needle (e.g., Huber needle) to inject the fluid through an implanted injection port that is coupled with the bladder. Similarly, fluid may be removed from the bladder by using a syringe and needle to withdraw the fluid through the implanted injection port.

In addition to or as an alternative to an injection port, a gastric band system may include a pump that is used to adjust the level of fluid in the bladder of the gastric band. An example of a gastric band system incorporating a pump is described in U.S. Pat. No. 7,390,294, entitled "Piezo Electrically Driven Bellows Infuser for Hydraulically Controlling an Adjustable Gastric Band," issued Jun. 24, 2008, the disclosure of which is incorporated by reference herein. Other examples of such a system are described in U.S. Pat. No. 7,351,240, entitled "Thermodynamically Driven Reversible Infuser Pump for Use as a Remotely Controlled Gastric Band," issued Apr. 1, 2008, the disclosure of which is incorporated by reference herein.

Other methods and devices to treat morbid obesity or other conditions include the use of gastric sleeves, gastric valves, space occupying devices, and bulking devices. Gastric sleeves may be placed within an interior portion of the stomach (or elsewhere within the gastrointestinal tract) instead of being placed about an exterior of the stomach. Some types of gastric sleeves may also be configured to restrict the absorption of nutrients within the gastrointestinal tract (e.g., within the duodenum). Examples of gastric sleeves are disclosed in U.S. Pat. No. 7,037,344, entitled "Apparatus and Methods for Treatment of Morbid Obesity," issued May 2, 2006, the disclosure of which is incorporated by reference herein.

Gastric valves may be placed inside or outside the stomach (e.g., at the esophagus or pylorus, etc.) and may selectively restrict the flow of food into the stomach. Like a gastric band, the degree of restriction provided by a gastric valve may be based at least in part on an amount of fluid in one or more inflatable portions of the gastric valve. Such a fluid level may be adjusted in a variety of ways. Examples of gastric valves are disclosed in U.S. Pub. No. 2006/0235448, entitled "Artificial Gastric Valve," published Oct. 19, 2006, the disclosure of which is incorporated by reference herein.

Space occupying devices may include a device such as a balloon that is implanted in the stomach. The space occupying balloon may be substantially non-digestable, and its presence in the stomach may lead to relatively early satiety. The amount of space occupied by the balloon may be based at least in part on an amount of fluid in the balloon. Such a fluid level may be adjusted in a variety of ways. In addition to occupying space within the stomach, a space occupying device may even form a restriction within the stomach by providing a relatively narrow passageway for passage of food, with the size of the passageway being based at least in part on an amount of fluid in the space occupying device. Examples of space occupying devices are disclosed in U.S. Pub. No. 2008/0103593, entitled "Use of Biosurgical Adhesive on Inflatable Device for Gastric Restriction," published May 1, 2008, the disclosure of which is incorporated by reference herein.

Bulking devices may include a device that is placed between layers of the stomach to reduce the internal volume or capacity of the stomach. Like a space occupying device, presence of a bulking device in the stomach may lead to relatively early satiety, and the amount of volume reduced by the presence of the bulking device may be based at least in part on an amount of fluid in the bulking device. In addition or in the alternative, a bulking device may be placed between layers of the esophagus to restrict the flow of food into the stomach. Examples of an adhesive being used as a bulking device are disclosed in U.S. Pub. No. 2008/0154228, entitled "Use of Biosurgical Adhesive as Bulking Agent," published Jun. 26, 2008, the disclosure of which is incorporated by reference herein, though it should be understood that such an adhesive may be replaced or supplemented with one or more inflatable members. Additional examples of bulking are disclosed in U.S. Pub. No. 2006/0247768, entitled "Bulking of Upper Esophageal Sphincter for Treatment of Obesity," published Nov. 2, 2006, the disclosure of which is incorporated by reference herein.

It should also be understood that the above-described devices to treat morbid obesity or other conditions may lack a fluid filled member, such that the devices may be adjusted using some method other than adjusting the amount or pressure of fluid in the device. For instance, such devices may be adjusted on a mechanical or electromechanical, non-hydraulic basis.

Hydrogels have also been used in a variety of biomedical applications. For instance, examples of such uses are described in Peppas, *Hydrogels in Medicine and Pharmacy*, CRC Press, Boca Raton, Fla. (1986); and Hoffman, "Hydrogels for Biomedical Applications," *Adv. Drug Deliv. Revs.*, 54, 3-12 (2002). Hydrogels may be configured to respond to changing conditions in their environment, such as temperature, pH, electric fields, ionic strength, the presence of a liquid, chemical stimuli, etc. Examples of environmentally responsive hydrogels (and uses thereof) are described in Peppas, "Physiologically Responsive Gels," *J. Bioact. Compat. Polym.*, 6, 241-246 (1991); Qiu, et al., "Environment-Sensitive Hydrogels for Drug Delivery," *Adv. Drug Deliv. Revs.*, 53, 321-339 (2001); Byrne, et al., "Molecular Imprinting within Hydrogels," *Adv. Drug Deliv. Revs.*, 54, 149-161 (2002); Jeong, et al., "Thermosenstive Sol-Gel Reversible Hydrogels," *Adv. Drug Deliv. Revs.*, 54, 37-51 (2002); and Miyata, et al., "Biomolecule-Sensitive Hydrogels," *Adv. Drug Deliv. Revs.*, 54, 79-98 (2002).

Physiological changes of the digestive system between fasting and consumption may be described in terms of changes in gastric acidity as measured using pH (the log concentration of hydronium ion concentration, or log $[H^+]$). The pH scale spans from 1 (acidic) to 14 (basic), with 7.0 being neutral. During the fasting state, the stomach pH may be relatively low (acidic). With meal ingestion, intragastric acidity may be buffered, with an elevation of gastric pH. The change in pH may occur rapidly with the initiation of consumption as food enters into the stomach. This change may also occur even in light of the secretion of gastric acids continuously during consumption. The buffering capacity of foods, including acidic or "spicy" foods, may be sufficient to provide a significant change in gastric pH.

Some examples described below relate to the use of a hydrogel to make adjustments in a method or device for treating morbid obesity in accordance with changes in environmental conditions within a patient. While a variety of devices and methods have been made and used to treat morbid obesity, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
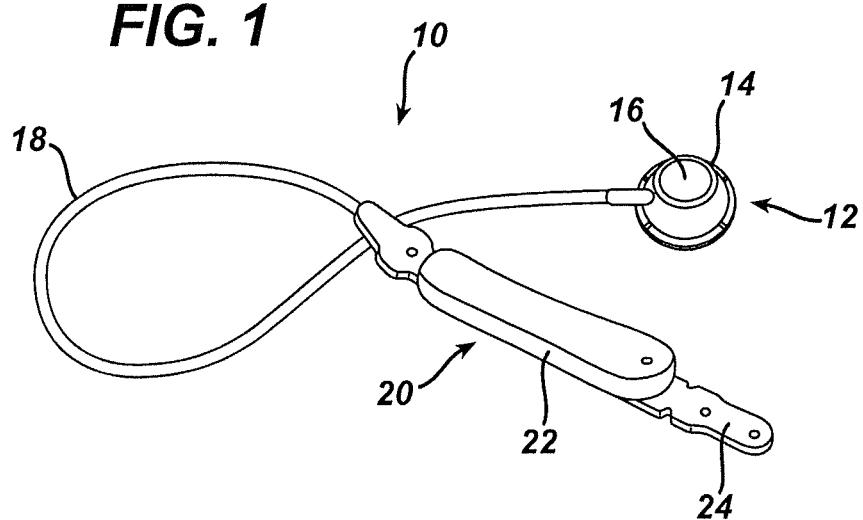
FIG. 1 depicts a perspective view of an implantable portion of an exemplary gastric band system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Overview

In some settings, it may be desirable to provide a morbid obesity treatment method or device that is dynamically responsive to physiological parameters of a patient. For instance, it may be desirable in some settings to provide a trigger system in which a physical and/or chemical change in a patient produces a dynamically responsive change in a morbid obesity treatment device. Several examples of such morbid obesity treatments and devices will be described in greater detail below, though it should be understood that the following examples are merely illustrative. While the main example is described in the context of an adjustable gastric band system, it should be understood that the same teachings may be readily incorporated into various other devices for treating morbid obesity, including but not limited to gastric sleeves, gastric valves, space occupying devices, and bulking devices as described above and as described elsewhere herein. Various alternative ways in which the present teachings may be incorporated into gastric bands, gastric sleeves, gastric valves, space occupying devices, and bulking devices will be apparent to those of ordinary skill in the art in view of the teachings herein.

Similarly, the following examples include the use of pH levels within a patient's stomach as the basis for triggering a dynamic response from a morbid obesity treatment device. However, it should be understood that any other types of physical and/or chemical changes in a patient may be used as a basis for triggering a dynamic response from a device. By way of example only, such changes may include gastric motility (e.g., as a physical stimulus to trigger a response) that changes and cycles with various stages of fasting and consumption; respiration (e.g., as a physical stimulus based on changes in diaphragm to trigger a response) that changes and cycles with different levels or types of activity (e.g., rest, sleep, daily routine activities, etc.); and/or electrical activity via muscle activity associated with changes in motility, etc. Such alternative bases may be used in addition to or in lieu of the pH level within a patient's stomach; and/or such alternative bases may be used in combination with other bases. Various types of physical and/or chemical changes in a patient that may be used as a basis for triggering a dynamic response from a device will be apparent to those of ordinary skill in the art in view of the teachings herein.

Hydrogels

Most of the examples described explicitly herein use a hydrogel material in order to trigger a dynamic response in a device. In particular, examples described herein use an environmentally sensitive hydrogel as a sensor and/or actuation mechanism in a device. Examples of suitable hydrogels and suitable hydrogel properties will be briefly discussed before discussion of how hydrogels may be incorporated into a dynamically responsive device system.

The monomers used to fabricate functional polymer gel networks may exhibit a relatively large physical change in response to minute chemical or biological stimuli. The responsive materials may include polymers prepared from multifunctional acrylates, hydroxyethylmethacrylate (HEMA), elastomeric acrylates, and related monomers. Incorporation of an environmentally sensitive hydrogel into a device used as a sensor or actuation mechanism may also involve a non-responsive material. The non-responsive materials may be used to define the walls or boundaries of the responsive or active system and form structural components of permeable, semi-permeable, and/or impermeable flexible or rigid barriers. Non-responsive materials may be prepared from a wider variety of monomers and polymers.

Environmentally sensitive hydrogels that may be used in the examples described herein may include those that demonstrate a reversible pH-dependent swelling behavior. These pH-sensitive hydrogels may be based on ionic networks. Anionic networks contain acidic pendant groups, such as carboxylic acid, with a characteristic $pK_a$; while cationic networks contain basic pendant groups, such as amine groups, with a characteristic $pK_b$. In the case of anionic networks, ionization of these acid groups may occur once the pH of the environment is above the acid group's characteristic $pK_a$. With deprotonation of the acid groups, the network may have fixed charges on its chains resulting in an electrostatic repulsion between the chains and, in addition, an increased hydrophilicity of the network. Because of these alterations in the network, water may be absorbed into the polymer to a greater degree causing swelling of the polymer.

A biological signal or parameter that triggers a response from a hydrogel may be a chemical species. Where the chemical species is the hydrogen ion, the state of swelling of the hydrogel network may be impacted as a function of the pKa or pKb with respect to the hydrogen ion concentration or the pH of the surrounding fluid or environment of the hydrogel. In some such cases, hydrogel polymer is a cross-linked network of hydrophilic monomers taken from the group consisting of unsaturated organic acid monomers, acrylic substituted alcohols, and acrylamides. More particularly, the monomers may be taken from the group consisting of methacrylic acids, acrylic acids, glycerolacrylate, glycerolmethacryulate, 2-hydroxyethylmethacrylate, 2-hydroxyethylacrylate, 2-(dimethylaminoethyl methacrylate, N-vinyl pyrrolidone, methacrylamide, and N,N-dimethylacrylamide poly(methacrylic acid) containing amounts of poly(ethylene glycol) n dimethacrylate, where n is the average molecular weight of the PEG chain. Alternatively, any other suitable type of hydrogel may be used.

When a hydrogel polymer is configured to swell in response to pH levels, this volume change can be considerable. By way of example only, some hydrogel polymers may be capable of changing volume on the order of 300% to 400%, or even on the order of 600%. The driving force or potential to undergo the change in volume may be significant, resulting in high expansion forces if the hydrogel is constrained during the expansion phase. Thus, as will be described in greater detail below, these expansion forces may be harnessed or otherwise be used to trigger a response in a morbid obesity treatment device.

While the following examples include the use of hydrogels to trigger a dynamic response in a device, it should be understood that such responses may be triggered in a variety of other ways. For instance, one or more electronic and/or chemical based sensors may be used to trigger a response in a device, in addition to or in lieu of using a hydrogel to trigger a response. By way of example only, one or more electrorheological fluids (sometimes referred to as ER fluids), which change their viscosity (e.g., from liquid to gel and back) in response to electrical fields or currents, may be used to trigger a dynamic response in a device. Merely illustrative examples of such ER fluids may include starch solutions, though any other suitable type of ER fluid may be used. Still other suitable types of materials and/or devices, etc., including combinations thereof, that may be used to trigger a dynamic response in a device such as a gastric band, etc., will be apparent to those of ordinary skill in the art in view of the teachings herein.

Hydrogel Pump for Gastric Band

FIGS. 1-4 illustrate an exemplary gastric band system (10). As shown, gastric band system (10) comprises an injection port (12), a gastric band (20), and a catheter (18), which together form a closed fluid circuit. Injection port (12) of the present example comprises a housing (14) and a needle penetrable septum (16). Housing (14) defines a fluid reservoir (not shown), such that a needle may pierce septum (16) to reach the reservoir and add or withdraw fluid (e.g., saline, etc.) as described in greater detail below. Housing (14) may be formed of titanium, plastic, or any other suitable material or combination of materials. Septum (16) may be formed of silicone or any other suitable material or combination of materials. Injection port (12) may be subcutaneously secured over a patient's sternum, to the patient's abdominal fascia, or in any other suitable location. Injection port (12) may be secured at approximately 10 cm below the surface of the patient's skin or at any other suitable depth. In some versions, injection port (12) is configured and operable in accordance with the teachings of U.S. Pub. No. 2005/0283118, entitled "Implantable Medical Device with Simultaneous Attachment Mechanism and Method," published Dec. 22, 2005, the disclosure of which is incorporated by reference herein. Alternatively, injection port (12) may have any other suitable configuration and/or operability.

Gastric band (20) of the present example comprises an inflatable bladder (22) that is secured to a flexible strap (24). Inflatable bladder (22) may be formed of silicone or any other suitable material or combination of materials. Catheter (18) provides fluid communication between bladder (22) and the reservoir of injection port (12). Accordingly, a needle that is inserted through septum (16) may be used to add or withdraw fluid from inflatable bladder (22), to adjust the restriction created by gastric band (20). In some versions, gastric band (20) is configured and operable in accordance with the teachings of U.S. Pat. No. 7,416,528, entitled "Latching Device for Gastric Band," issued Aug. 26, 2008, the disclosure of which is incorporated by reference herein. Alternatively, gastric band (20) may have any other suitable configuration and/or operability.

Figure 2:
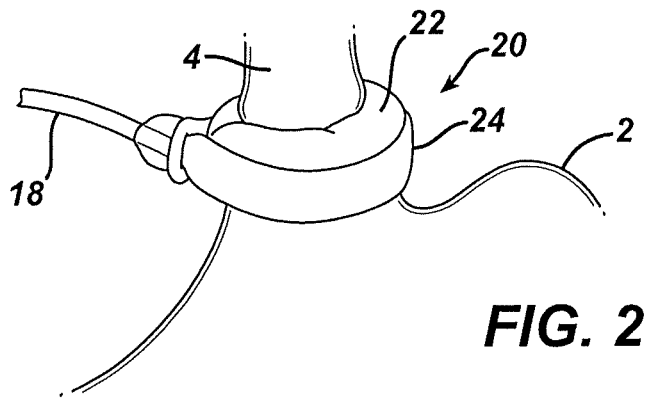
FIG. 2 depicts a perspective view of the gastric band of FIG. 1, showing the band positioned around the gastro-esophageal junction of a patient.

In some settings, gastric band (20) is applied about the gastro-esophageal junction of a patient. In particular, and as shown in FIG. 2, gastric band (20) is installed such that bladder (22) is adjacent to the tissue of the gastro-esophageal junction, with strap (24) on the outside of bladder (22). The ends of strap (24) are secured relative to each other when gastric band (20) is sufficiently wrapped about the patient's stomach (2). While strap (24) is flexible in this example, strap (24) substantially resists stretching along its length. Accordingly, when fluid is added to bladder (22) (e.g., using a needle inserted through septum (16) of injection port (12), etc.), bladder (22) expands and exerts inward forces on the gastro-esophageal junction of the patient. This reduces the size of the internal stoma at the gastro-esophageal junction, thereby creating a restriction on food intake into the patient's stomach (2). It should be understood that the size of this stoma may be decreased by adding more fluid to bladder (22) to create a greater degree of restriction; or increased by withdrawing fluid from bladder (22) to reduce the degree of restriction.

Figure 3:
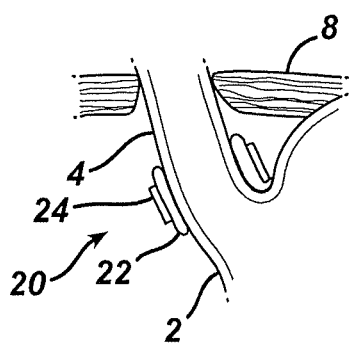
FIG. 3 depicts a cross-sectional view of the gastric band of FIG. 1, showing the band positioned around the gastro-esophageal junction of a patient in a deflated configuration.
Figure 4:
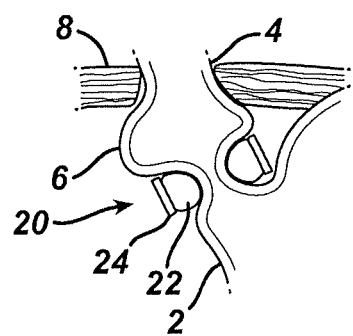
FIG. 4 depicts a cross-sectional view of the gastric band of FIG. 1, showing the band positioned around the gastro-esophageal junction of a patient in an inflated configuration to create a food intake restriction.

As shown in FIGS. 2-4, an installed gastric band (20) at least substantially encloses the upper portion of stomach (2) near the junction with esophagus (4) in the present example. FIG. 3 shows gastric band (20) in a deflated configuration, where bladder (22) contains little to no fluid, thereby maximizing the size of the stoma opening into stomach (2). FIG. 4 shows gastric band (20) in an inflated, fluid-filled configuration, where bladder (22) contains substantially more fluid than is shown in FIG. 3. In this configuration shown in FIG. 4, the pressure of gastric band (20) against stomach (2) is increased due to the fluid within bladder (22), thereby decreasing the stoma opening to create a food intake restriction. FIG. 4 also schematically illustrates the dilation of esophagus (4) above gastric band (20) to form an upper pouch (6) beneath the diaphragm muscle (8) of the patient. After gastric band system (10) has been implanted in the patient and an initial amount of fluid (e.g., saline, etc.) has been introduced to gastric band system (10), a physician may need to occasionally adjust the amount of fluid in gastric band system (10) by using a needle (e.g., Huber needle, etc.) that is inserted through septum (16) of injection port (12). For instance, such adjustments may be desirable to account for weight loss achieved by the patient, and may be started around one month (or any other suitable time period) after gastric band system (10) has been implanted.

Figure 5A:
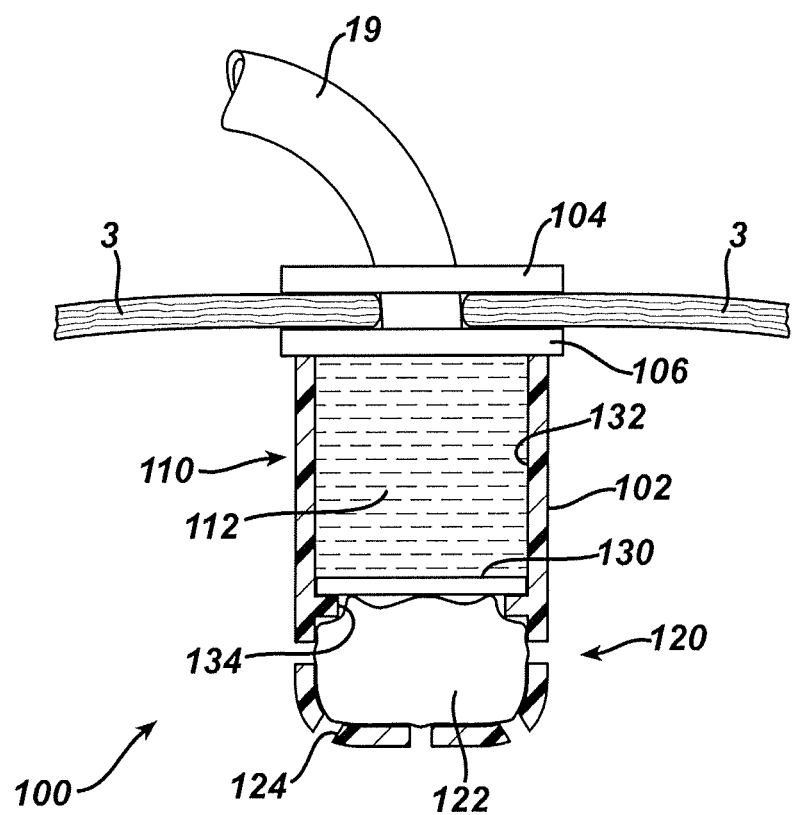
FIG. 5A depicts a schematic view of an exemplary hydrogel pump that may be used with the gastric band of FIG. 1, with the hydrogel in a collapsed state.
Figure 5B:
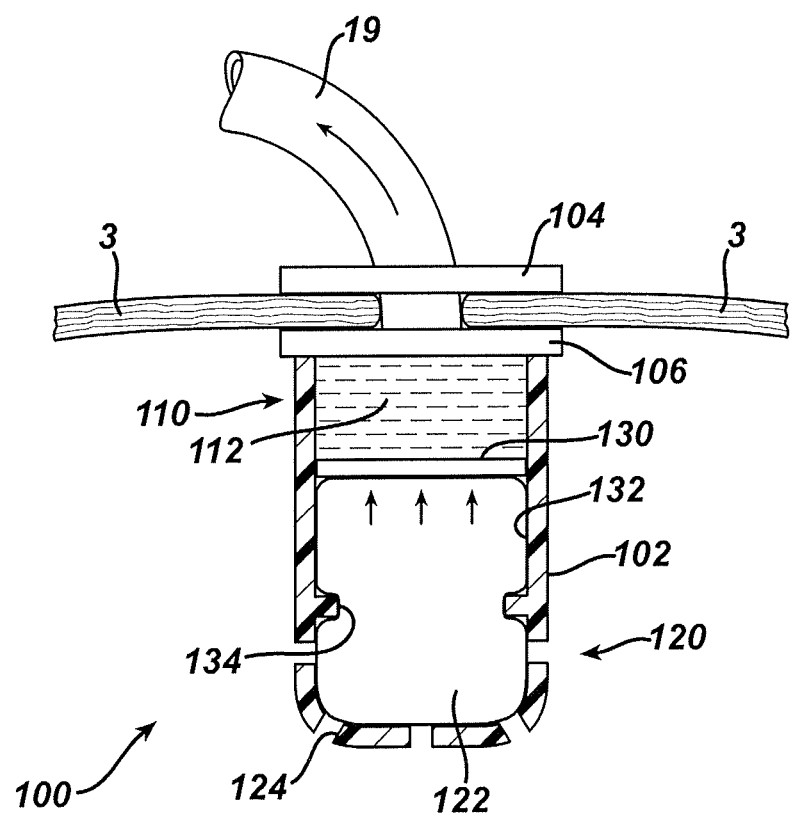
FIG. 5B depicts a schematic view of the hydrogel pump of FIG. 5A, with the hydrogel in an expanded state.

In some scenarios, it may be desirable to only expand gastric band (20) to the expanded state shown in FIG. 4 when a patient is eating; and to allow gastric band (20) to return to the collapsed state shown in FIG. 3 when the patient is fasting or otherwise not eating. It may therefore be desirable in some settings to provide a pump that is configured to change the state of a gastric band (20) based on whether the patient is eating. FIGS. 5A-5B illustrate an exemplary hydrogel pump (100) that may be incorporated into gastric band system (10). In particular, hydrogel pump (100) may be in fluid communication with a catheter (19) that is coupled with catheter (18) of gastric band system (10). For instance, catheter (19) may be joined with catheter (18) by a conventional "T" or "Y" coupling or in any other suitable fashion. Alternatively, catheter (19) may be joined directly with bladder (22) of gastric band (20), may be joined directly with injection port (12), or may be otherwise incorporated into gastric band system (10). While hydrogel pump (100) is in fluid communication with gastric band system (10) in the present example, hydrogel pump (100) and gastric band system (10) together still form a closed fluid circuit like the gastric band system (10) shown in FIG. 1.

As shown, hydrogel pump (100) comprises a housing (102) that is secured to the wall (3) of a patient's stomach (2). In particular, hydrogel pump (100) is secured within the interior of the patient's stomach (2), with catheter (19) extending exteriorly from the patient's stomach (2) to couple with gastric band system (10). By way of example only, housing (102) may be secured in the lower/distal region of the patient's stomach (2), though any other suitable location or locations may be used. Catheter (19) is fed through an opening formed in the wall (3) of the patient's stomach (2), and a pair of flanges (104, 106) are secured to opposite faces of the wall (3) adjacent to this opening. Flanges (104, 106) seal against catheter (19) and against the opposite faces of the wall (3), such that fluids may not leak through the interface between flanges (104, 106) and catheter (19), and such that fluids may not leak through the interface between flanges (104, 106) and wall (3). In other words, the inner lumen of catheter (19) is the only path for fluid communication through wall (3) in the present example. Flanges (104, 106) may be sealed to wall (3) using one or more biosurgical adhesives (e.g., cyanoacrylate, isocyanate, etc.) and/or using any other suitable devices, substances, or techniques. Flanges (104, 106) may also be sealed to catheter (19) in any suitable fashion. Flange (106) may form a lid of housing (102), such that flange (106) is also sealed to housing (102).

Housing (102) of the present example is formed of a substantially rigid material that can substantially withstand acid and other fluids in the stomach (2), grinding and churning mechanisms of gastric motility, and enzymatic attack by digestive enzymes. For instance, housing (102) may be formed of a biocompatible plastic, metal, or any other suitable material or combination of materials. Housing (102) includes an upper section (110) and a lower section (120). While housing (102) is shown in cross-section in FIGS. 5A-5B, it should be understood that housing (102) may have any suitable shape, including but not limited to cylindraceous. Upper section (110) and lower section (120) are separated by a piston disc (130) in the present example. A fluid (112) such as saline is provided in upper section (110), and is in fluid communication with gastric band system (10) via catheter (19). In the present example, with piston disc (130) in the lowered position shown in FIG. 5A, upper section (110) has a fluid capacity of approximately two cc's. Alternatively, upper section (110) may have any other suitable fluid capacity.

An environmentally sensitive hydrogel (122) is provided in lower section (120) of housing (120). Piston disc (130) substantially seals against the inner wall (132) of housing (102), such that piston disc (130) fluidly isolates upper section (110) from lower section (120). Piston disc (130) is movable along the longitudinal axis defined by housing (102), to expel fluid (112) from upper section (110) as will be described in greater detail below. Piston disc (130) maintains the seal between upper section (110) and lower section (120) even during and after such movement within housing (110). A rim (134) protrudes radially inwardly from inner wall (132) of housing, and presents an inner diameter that is less than the outer diameter of piston disc (130). Rim (134) thus restricts downward movement of piston disc (130), such that piston disc (130) may not move lower than the position shown in FIG. 5A. Of course, as with other features described herein, rim (134) is merely optional.

Lower section (120) of housing (102) has a plurality of openings (124) formed therein, such that gastric fluids may enter and leave lower section (120) of housing (102) freely to allow changing physiological conditions occurring in stomach (2) (e.g., relating to consumption and fasting) to also occur inside lower section (120) of housing (102). Accordingly, hydrogel (122) is in fluid communication with the interior of stomach (2) via openings (124) in the present example. In addition, hydrogel (122) of the present example is formulated and configured such that it is in a collapsed state in a low pH environment (FIG. 5A); and such that it will swell and expand in response to an increased pH level (FIG. 5B). Those of ordinary skill in the art will recognize that an increase in pH may be caused when the patient begins to consume food, and that the pH level in the stomach (2) may go down when the patient is fasting or otherwise not consuming food. By way of example only, hydrogel (122) may be formulated and configured such that it swells to an expanded state (FIG. 5B) when it is exposed to a pH level that is at or greater than approximately 4 (or at or greater than approximately 5); and such that it will be in the collapsed state (FIG. 5A) when it is exposed to a pH level that is less than approximately 4 (or less than approximately 5). Alternatively, hydrogel (122) may be formulated and configured such that it swells or shrinks in response to any other suitable pH levels. When hydrogel (122) swells in the present example, it forces piston disc (130) upwardly as shown in FIG. 5B, which in turn forces fluid (112) from upper section (110) of housing to gastric band system (10). Openings (124) are sized and configured such that swelling hydrogel (122) will favor forcing piston disc (130) upwardly over protruding through openings (124). Hydrogel (122) thus drives piston disc (130) based on the pH level of fluid within the patient's stomach (2). A particular hydrogel formulation and configuration may be selected such that the pressure imposed by swelling hydrogel (122) on piston disc (130) (FIG. 5B) provides a desired pressure of fluid (112) for gastric band system (10).

In view of the foregoing, it should be understood that before a patient begins consuming food, hydrogel (122) may be in the collapsed state shown in FIG. 5A. At this time, gastric band (20) may also be in the collapsed state shown in FIG. 3. As the patient begins to consume food, the pH level in the patient's stomach (2) begins to rise. This increase in pH is sensed by hydrogel (122) due to fluid in stomach (2) leaking into lower section (120) via openings (124). In response to this increase in pH, hydrogel (122) swells to the expanded state shown in FIG. 5B. This swelling drives piston disc (130) to a raised position, thereby forcing fluid (112) from upper section (110) of housing to gastric band system (10). Gastric band (20) then reaches the expanded state shown in FIG. 4, creating a restriction at the gastro-esophageal junction of a patient. After the patient is done eating, the patient's physiology eventually returns to the fasting stage, and the pH level in the patient's stomach decreases. This decrease in pH level causes hydrogel (122) to collapse back to the configuration shown in FIG. 5A. In addition, the pressure of fluid (112) in gastric band system (10) drives piston disc (130) back down to the position shown in FIG. 5A, such that fluid (112) is drained from gastric band system (10) into upper section (110) of housing (120), and such that gastric band (20) returns to the collapsed state shown in FIG. 3. Of course, a variety of features and components of hydrogel pump (100) may be modified, substituted, or supplemented in various ways; if not be omitted altogether. Numerous suitable variations of hydrogel pump (100) will be apparent to those of ordinary skill in the art in view of the teachings herein.

In a merely illustrative variation of hydrogel pump (100), the responsiveness of hydrogel (122) to pH levels is reversed. In particular, hydrogel (122) is configured to expand in response to a low pH level (FIG. 5A) and collapse in response to a high pH level (FIG. 5B). Such a reversed response may be suitable in a scenario where gastric band (20) is being used to treat gastroesophageal reflux disease (GERD) or some other condition (e.g., rather than being used to treat morbid obesity). In some such versions, pump (100) may be placed closer to the patient's esophagus (4) or in some other suitable location where it could provide a response to an occurrence of undesired acid reflux. By constricting a band (20) in response to an occurrence of undesired acid reflux, the likelihood of harm caused by such acid reflux may be reduced.

As another merely illustrative variation of hydrogel pump (100), hydrogel pump (100) may be coupled with a gastric valve to drive the valve between substantially restrictive and substantially non-restrictive configurations. For instance, hydrogel pump (100) may be coupled with a gastric valve as described in U.S. Pub. No. 2006/0235448, entitled "Artificial Gastric Valve," published Oct. 19, 2006, the disclosure of which is incorporated by reference herein. Various suitable ways in which hydrogel pump (100) may be coupled with such a gastric valve will be apparent to those of ordinary skill in the art in view of the teachings herein. Still other suitable ways in which a hydrogel pump (100) (or variations thereof) may be used will also be apparent to those of ordinary skill in the art in view of the teachings herein.

Shrinking Hydrogel Fluid Reservoir to Actuate Gastric Band

Figure 6A:
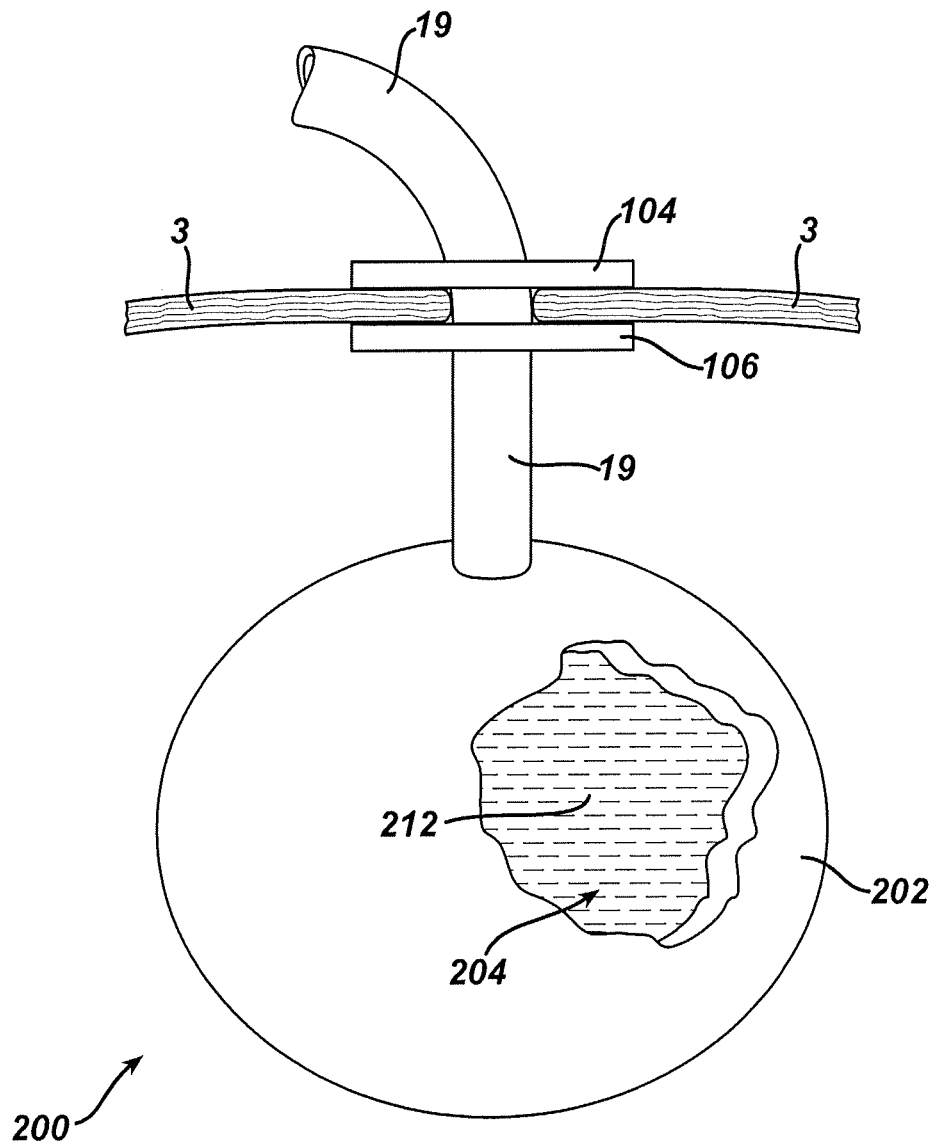
FIG. 6A depicts a schematic view of an exemplary hydrogel fluid reservoir that may be used with the gastric band of FIG. 1, with the hydrogel in an expanded state, and with a portion of the hydrogel removed to show a hollow interior.
Figure 6B:
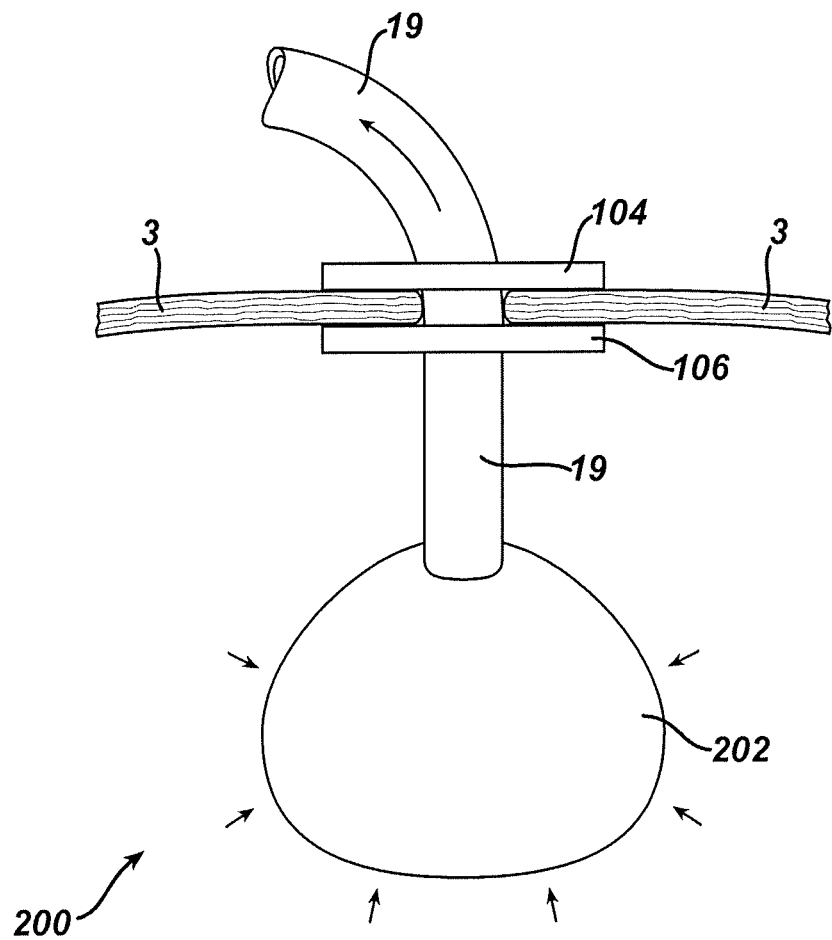
FIG. 6B depicts a schematic view of the hydrogel fluid reservoir of FIG. 6A, with the hydrogel in a collapsed state.

FIGS. 6A-6B show an exemplary hydrogel fluid reservoir (200) that may be incorporated into a gastric band system (10). Hydrogel fluid reservoir (200) may thus be used as an alternative to hydrogel pump (100) described above. In particular, hydrogel fluid reservoir (200) may be in fluid communication with a catheter (19) that is coupled with catheter (18) of gastric band system (10). For instance, catheter (19) may be joined with catheter (18) by a conventional "T" or "Y" coupling or in any other suitable fashion. Alternatively, catheter (19) may be joined directly with bladder (22) of gastric band (20), may be joined directly with injection port (12), or may be otherwise incorporated into gastric band system (10). While hydrogel fluid reservoir (200) is in fluid communication with gastric band system (10) in the present example, hydrogel fluid reservoir (200) and gastric band system (10) together still form a closed fluid circuit like the gastric band system (10) shown in FIG. 1.

As shown, hydrogel fluid reservoir (200) comprises a hollow sphere formed of hydrogel (202). While hydrogel (202) is formed as a sphere in this example, it should be understood that any other suitable shape may be used. Hydrogel sphere (202) is secured to the wall (3) of a patient's stomach (2). In particular, hydrogel sphere (202) is secured within the interior of the patient's stomach (2), with catheter (19) extending exteriorly from the patient's stomach (2) to couple with gastric band system (10). By way of example only, sphere (202) may be secured in the lower/distal region of the patient's stomach (2), though any other suitable location or locations may be used. Catheter (19) is fed through an opening formed in the wall (3) of the patient's stomach (2), and a pair of flanges (104, 106) are secured to opposite faces of the wall (3) adjacent to this opening Flanges (104, 106) may be configured the same as is described above with respect to hydrogel pump (100); or may have any other suitable configuration. The inner lumen of catheter (19) is the only path for fluid communication through wall (3) in the present example. Hydrogel sphere (202) defines a hollow interior (204) or reservoir, within which resides a fluid (212) (e.g., saline, etc.). Hollow interior (204) and fluid (212) are in communication with catheter (19), such that fluid (212) may be forced toward gastric band (20) via catheter (19) when hydrogel sphere (202) collapses as described in greater detail below.

In the present example, hydrogel sphere (202) is formed entirely of hydrogel. In some other versions, the hollow interior (204) is lined with silicone or some other material (not shown), such as to fluidly isolate fluid (212) from hydrogel (202). In addition or in the alternative, a jacket or case (not shown) may be provided about the exterior of hydrogel sphere (202). Such a jacket or case may be porous, have openings formed in it, or otherwise permit fluids in stomach (2) to contact hydrogel (202). Providing such components inside and/or outside of hydrogel sphere (202) may increase the structural integrity of hydrogel sphere (202), while still permitting hydrogel sphere (202) to expand or contract as described in greater detail below. Furthermore, in some variations, a jacket provided on the exterior of hydrogel sphere (202) is substantially resilient in addition to being porous. For instance, such a resilient jacket may be resiliently biased to a shrunk position, similar to what is shown in FIG. 6B. In some such versions, the resilient jacket is stretched against its bias when hydrogel sphere (202) is in the expanded configuration shown in FIG. 6A; and the resilient bias of jacket assists hydrogel sphere (202) to reach the collapsed configuration shown in FIG. 6B. Alternatively, the resilient jacket may simply travel with hydrogel sphere (202) to the collapsed configuration shown in FIG. 6B, without necessarily assisting hydrogel sphere (202) in reaching the collapsed configuration. Other various alternative ways in which hydrogel sphere (202) may be configured, including but not limited to other components that may be provided on or within hydrogel sphere (202), will be apparent to those of ordinary skill in the art in view of the teachings herein. Similarly, various ways in which catheter (19) may be coupled with hydrogel sphere (202) will be apparent to those of ordinary skill in the art in view of the teachings herein.

The hydrogel that forms hydrogel sphere (202) in the present example is environmentally sensitive, such that hydrogel sphere (202) will change between a swelled state (FIG. 6A) and a collapsed state (FIG. 6B). In particular, the hydrogel of hydrogel sphere (202) is formulated and configured such that it is in an expanded state in a low pH environment (FIG. 6A); and such that it will collapse in response to an increased pH level (FIG. 6B). Those of ordinary skill in the art will recognize that an increase in pH may be caused when the patient begins to consume food, and that the pH level in the stomach (2) may go down when the patient is fasting or otherwise not consuming food. By way of example only, hydrogel sphere (202) may be formulated and configured such that it shrinks to a collapsed state (FIG. 6B) when it is exposed to a pH level that is at or greater than approximately 4 (or at or greater than approximately 5); and such that it swells to an expanded state (FIG. 6A) when it is exposed to a pH level that is less than approximately 4 (or less than approximately 5). Alternatively, hydrogel sphere (202) may be formulated and configured such that it swells or shrinks in response to any other suitable pH levels.

When hydrogel sphere (202) is in the expanded state as shown in FIG. 6A, its hollow interior (204) provides a reservoir having a capacity of approximately two cc's. Alternatively, hollow interior (204) of expanded hydrogel sphere (202) may have any other suitable capacity. When hydrogel sphere (202) shrinks to the collapsed state as shown in FIG. 6B, the capacity of the reservoir provided by hollow interior (204) is reduced, which in turn forces fluid (212) from hollow interior (204) to gastric band system (10). Hydrogel sphere (202) thus drives fluid (212) from hollow interior (204) toward gastric band system (10) based on the pH level of fluid within the patient's stomach (2). A particular hydrogel formulation and configuration may be selected such that the pressure imposed by shrinking hydrogel sphere (202) on fluid (212) (FIG. 6B) provides a desired pressure of fluid (212) for gastric band system (10).

In view of the foregoing, it should be understood that before a patient begins consuming food, hydrogel sphere (202) may be in the expanded state shown in FIG. 6A. At this time, gastric band (20) may also be in the collapsed state shown in FIG. 3. As the patient begins to consume food, the pH level in the patient's stomach (2) begins to rise. This increase in pH is sensed by hydrogel sphere (202) due to fluid in stomach (2) communicating with hydrogel sphere (202). In response to this increase in pH, hydrogel sphere (202) shrinks to the collapsed state shown in FIG. 6B. This shrinking reduces the capacity of hollow interior (204), thereby forcing fluid (212) from hydrogel sphere (202) to gastric band system (10). Gastric band (20) then reaches the expanded state shown in FIG. 4, creating a restriction at the gastro-esophageal junction of a patient. After the patient is done eating, the patient's physiology eventually returns to the fasting stage, and the pH level in the patient's stomach decreases. This decrease in pH level causes hydrogel sphere (202) to swell back to the expanded configuration shown in FIG. 6A, which in turn increases the capacity of the reservoir provided by hollow interior (204). In addition, the pressure of fluid (212) in gastric band system (10) urges fluid (212) back into hollow interior (204), such that fluid (212) is drained from gastric band system (10) into hollow interior (204), and such that gastric band (20) returns to the collapsed state shown in FIG. 3. Of course, a variety of features and components of hydrogel reservoir (200) may be modified, substituted, or supplemented in various ways; if not be omitted altogether. Numerous suitable variations of hydrogel reservoir (200) will be apparent to those of ordinary skill in the art in view of the teachings herein.

In a merely illustrative variation of hydrogel reservoir (200), the responsiveness of hydrogel sphere (202) to pH levels is reversed. In particular, hydrogel sphere (202) is configured to collapse in response to a low pH level (FIG. 6B) and swell in response to a high pH level (FIG. 6A). Such a reversed response may be suitable in a scenario where gastric band (20) is being used to treat gastroesophageal reflux disease (GERD) or some other condition (e.g., rather than being used to treat morbid obesity). In some such versions, reservoir (200) may be placed closer to the patient's esophagus (4) or in some other suitable location where it could provide a response to an occurrence of undesired acid reflux. By constricting a band (20) in response to an occurrence of undesired acid reflux, the likelihood of harm caused by such acid reflux may be reduced. Still other suitable ways in which a hydrogel reservoir (200) (or variations thereof) may be used will be apparent to those of ordinary skill in the art in view of the teachings herein.

Swelling Hydrogel in Fluid Reservoir to Actuate Gastric Band

Figure 7A:
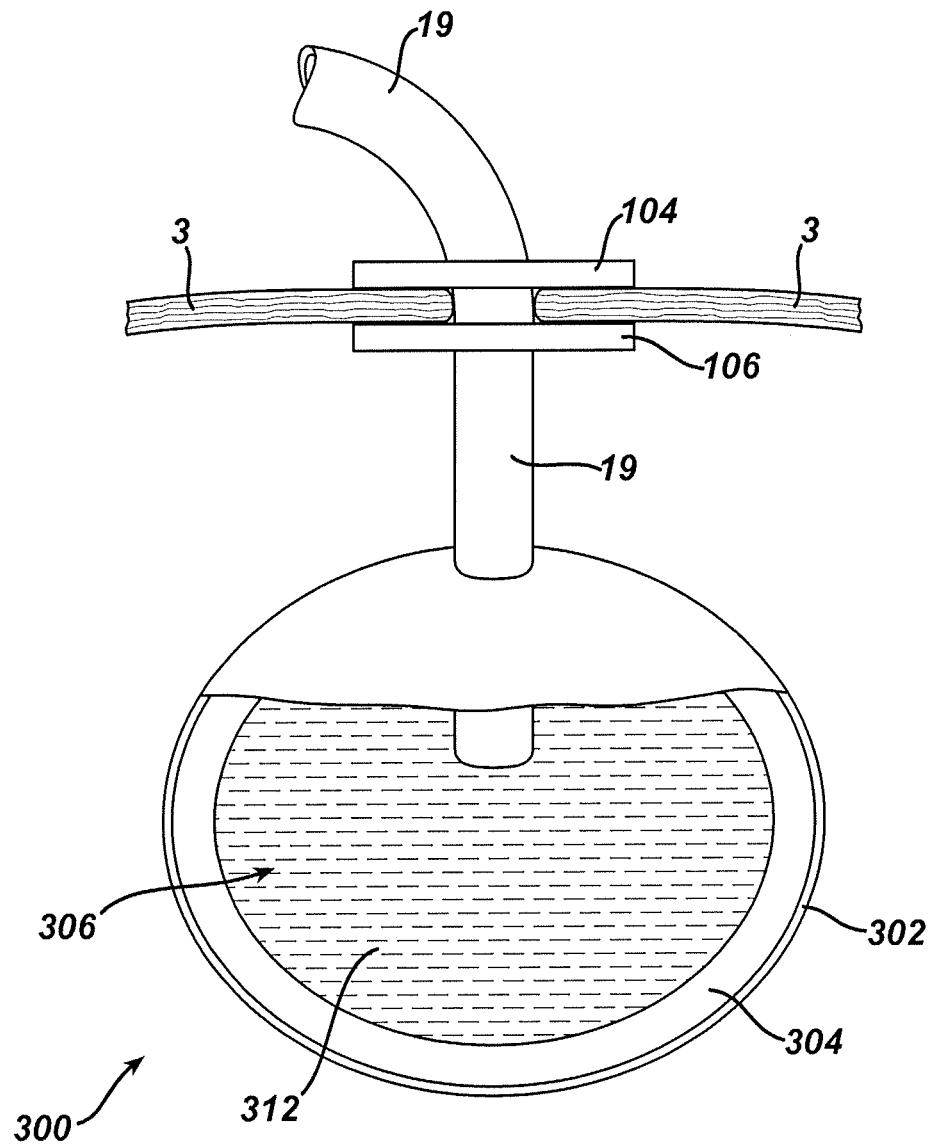
FIG. 7A depicts a schematic view of another exemplary hydrogel fluid reservoir that may be used with the gastric band of FIG. 1, with the hydrogel in a collapsed state, and with a portion of the reservoir removed to show a interior portions of the reservoir.
Figure 7B:
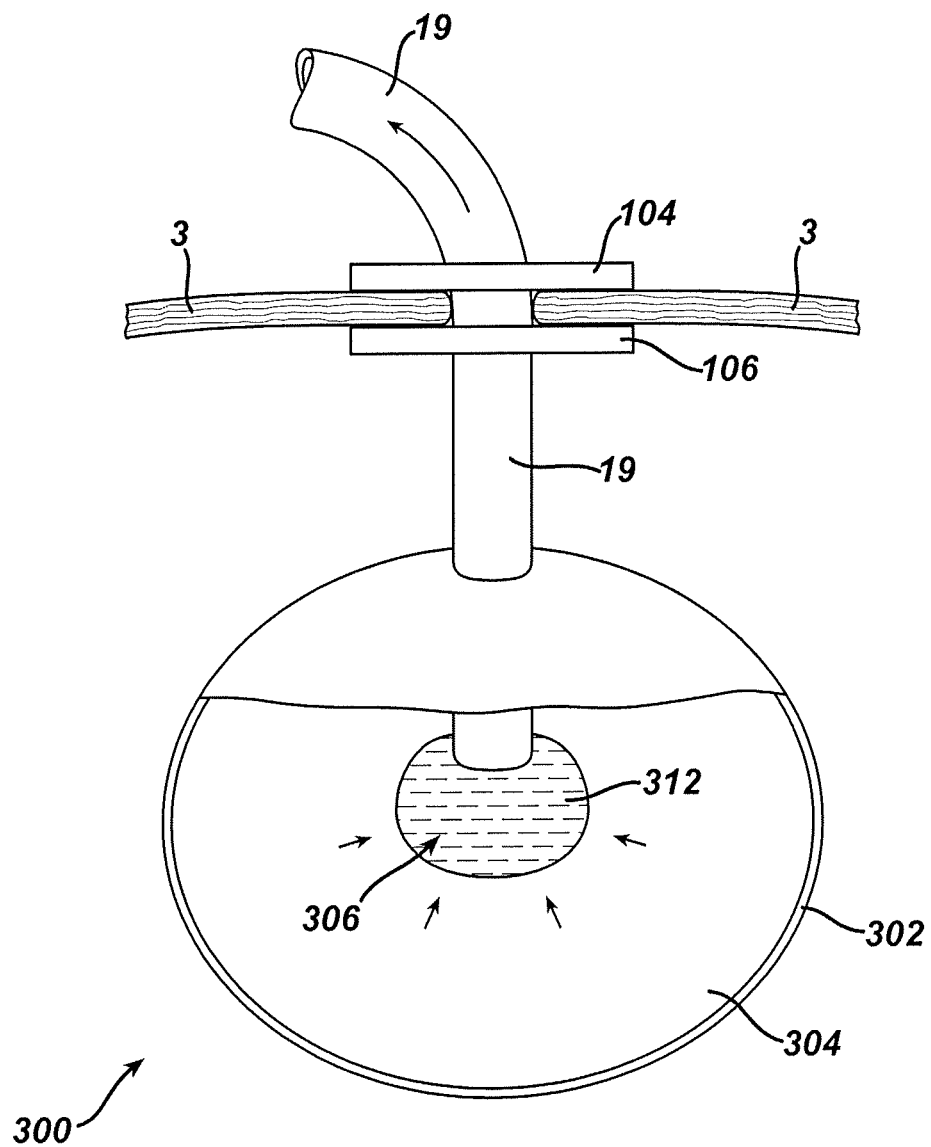
FIG. 7B depicts a schematic view of the hydrogel fluid reservoir of FIG. 7A, with the hydrogel in an expanded state, and with a portion of the reservoir removed to show interior portions of the reservoir.

FIGS. 7A-7B show another exemplary hydrogel fluid reservoir (300) that may be incorporated into a gastric band system (10). Hydrogel fluid reservoir (300) may thus be used as an alternative to hydrogel pump (100) and hydrogel fluid reservoir (200) described above. In particular, hydrogel fluid reservoir (300) may be in fluid communication with a catheter (19) that is coupled with catheter (18) of gastric band system (10). For instance, catheter (19) may be joined with catheter (18) by a conventional "T" or "Y" coupling or in any other suitable fashion. Alternatively, catheter (19) may be joined directly with bladder (22) of gastric band (20), may be joined directly with injection port (12), or may be otherwise incorporated into gastric band system (10). While hydrogel fluid reservoir (300) is in fluid communication with gastric band system (10) in the present example, hydrogel fluid reservoir (300) and gastric band system (10) together still form a closed fluid circuit like the gastric band system (10) shown in FIG. 1.

As shown, hydrogel fluid reservoir (300) comprises an outer jacket (302) encasing a hollow sphere formed of hydrogel (304). While hydrogel fluid reservoir (300) is formed as a sphere in this example, it should be understood that any other suitable shape may be used. Hydrogel fluid reservoir (300) is secured to the wall (3) of a patient's stomach (2). In particular, hydrogel fluid reservoir (300) is secured within the interior of the patient's stomach (2), with catheter (19) extending exteriorly from the patient's stomach (2) to couple with gastric band system (10). By way of example only, hydrogel fluid reservoir (300) may be secured in the lower/distal region of the patient's stomach (2), though any other suitable location or locations may be used. Catheter (19) is fed through an opening formed in the wall (3) of the patient's stomach (2), and a pair of flanges (104, 106) are secured to opposite faces of the wall (3) adjacent to this opening. Flanges (104, 106) may be configured the same as is described above with respect to hydrogel pump (100); or may have any other suitable configuration. The inner lumen of catheter (19) is the only path for fluid communication through wall (3) in the present example Hydrogel sphere (304) defines a hollow interior (306) or reservoir, within which resides a fluid (312) (e.g., saline, etc.). Hollow interior (306) and fluid (312) are in communication with catheter (19), such that fluid (312) may be forced toward gastric band (20) via catheter (19) when the hydrogel forming hydrogel sphere (302) expands as described in greater detail below.

In the present example, jacket (302) is formed of a porous, non-extensible material that can substantially withstand acid and other fluids in the stomach (2), grinding and churning mechanisms of gastric motility, and enzymatic attack by digestive enzymes. For instance, jacket (302) may be formed of a porous DACRON or polyester material, or any other suitable material or combination of materials, including but not limited to other materials referred to elsewhere herein. The porous property of jacket (302) permits fluids in stomach (2) to contact hydrogel (304), such that gastric fluids may enter and leave jacket (302) freely to allow changing physiological conditions occurring in stomach (2) (e.g., relating to consumption and fasting) to also occur inside jacket (302). Jacket (302) may have openings formed in it in addition to or as an alternative to being formed of a porous material. The non-extensible property of jacket (302) provides resistance to outward swelling of hydrogel sphere (304) as described in greater detail below. In some versions, the hollow interior (306) of hydrogel sphere (304) is lined with silicone or some other material (not shown), such as to fluidly isolate fluid (312) from hydrogel (304). Other various alternative ways in which hydrogel fluid reservoir (300) may be configured, including but not limited to other components that may be provided on or within hydrogel sphere (304), will be apparent to those of ordinary skill in the art in view of the teachings herein. Similarly, various ways in which catheter (19) may be coupled with hydrogel fluid reservoir (300) will be apparent to those of ordinary skill in the art in view of the teachings herein.

The hydrogel that forms hydrogel sphere (304) in the present example is environmentally sensitive, such that hydrogel sphere (304) will change between a collapsed state (FIG. 7A) and a swelled state (FIG. 7B). In particular, the hydrogel of hydrogel sphere (304) is formulated and configured such that it is in a collapsed state in a low pH environment (FIG. 7A); and such that it will swell in response to an increased pH level (FIG. 7B). Those of ordinary skill in the art will recognize that an increase in pH may be caused when the patient begins to consume food, and that the pH level in the stomach (2) may go down when the patient is fasting or otherwise not consuming food. By way of example only, hydrogel sphere (304) may be formulated and configured such that it swells to an expanded state (FIG. 7B) when it is exposed to a pH level that is at or greater than approximately 4 (or at or greater than approximately 5); and such that it shrinks to a collapsed state (FIG. 7A) when it is exposed to a pH level that is less than approximately 4 (or less than approximately 5). Alternatively, hydrogel sphere (304) may be formulated and configured such that it swells or shrinks in response to any other suitable pH levels.

When hydrogel sphere (304) is in the collapsed state as shown in FIG. 7A, its hollow interior (306) provides a reservoir having a capacity of approximately two cc's. Alternatively, hollow interior (306) of collapsed hydrogel sphere (304) may have any other suitable capacity. When hydrogel sphere (304) swells to the expanded state as shown in FIG. 7B, jacket (302) substantially prevents hydrogel sphere (304) from expanding outwardly, such that hydrogel sphere (304) expands inwardly. The capacity of the reservoir provided by hollow interior (306) is thereby reduced, which in turn forces fluid (312) from hollow interior (306) to gastric band system (10). Hydrogel sphere (304) thus drives fluid (312) from hollow interior (306) toward gastric band system (10) based on the pH level of fluid within the patient's stomach (2). A particular hydrogel formulation and configuration may be selected such that the pressure imposed by swelling hydrogel sphere (304) on fluid (312) (FIG. 7B) provides a desired pressure of fluid (312) for gastric band system (10).

In view of the foregoing, it should be understood that before a patient begins consuming food, hydrogel sphere (304) may be in the collapsed state shown in FIG. 7A. At this time, gastric band (20) may also be in the collapsed state shown in FIG. 3. As the patient begins to consume food, the pH level in the patient's stomach (2) begins to rise. This increase in pH is sensed by hydrogel sphere (304) due to fluid in stomach (2) communicating with hydrogel sphere (304) via jacket (302). In response to this increase in pH, hydrogel sphere (304) swells to the expanded state shown in FIG. 7B. The combination of this swelling by hydrogel sphere (304) and the non-extensibility of jacket (302) reduces the capacity of hollow interior (306), thereby forcing fluid (312) from hydrogel sphere (304) to gastric band system (10). Gastric band (20) then reaches the expanded state shown in FIG. 4, creating a restriction at the gastro-esophageal junction of a patient. After the patient is done eating, the patient's physiology eventually returns to the fasting stage, and the pH level in the patient's stomach decreases. This decrease in pH level causes hydrogel sphere (304) to shrink back to the collapsed configuration shown in FIG. 7A, which in turn increases the capacity of the reservoir provided by hollow interior (306). In addition, the pressure of fluid (312) in gastric band system (10) urges fluid (312) back into hollow interior (306), such that fluid (312) is drained from gastric band system (10) into hollow interior (306), and such that gastric band (20) returns to the collapsed state shown in FIG. 3. Of course, a variety of features and components of hydrogel reservoir (300) may be modified, substituted, or supplemented in various ways; if not be omitted altogether. Numerous suitable variations of hydrogel reservoir (300) will be apparent to those of ordinary skill in the art in view of the teachings herein.

In a merely illustrative variation of hydrogel reservoir (300), the responsiveness of hydrogel sphere (304) to pH levels is reversed. In particular, hydrogel sphere (304) is configured to swell in response to a low pH level (FIG. 7B) and shrink in response to a high pH level (FIG. 7A). Such a reversed response may be suitable in a scenario where gastric band (20) is being used to treat gastroesophageal reflux disease (GERD) or some other condition (e.g., rather than being used to treat morbid obesity). In some such versions, reservoir (300) may be placed closer to the patient's esophagus (4) or in some other suitable location where it could provide a response to an occurrence of undesired acid reflux. By constricting a band (20) in response to an occurrence of undesired acid reflux, the likelihood of harm caused by such acid reflux may be reduced. Still other suitable ways in which a hydrogel reservoir (300) (or variations thereof) may be used will be apparent to those of ordinary skill in the art in view of the teachings herein.

Hydrogel to Activate Electromechanical Pump

As noted above, some versions of a gastric band system (10) may include a pump that is operable to adjust the level of fluid in bladder (22) in gastric band (20). Merely illustrative examples of such pumps are described in U.S. Pat. No. 7,390,294, entitled "Piezo Electrically Driven Bellows Infuser for Hydraulically Controlling an Adjustable Gastric Band," issued Jun. 24, 2008, the disclosure of which is incorporated by reference herein. Other merely illustrative examples of such pumps are described in U.S. Pat. No. 7,351,240, entitled "Thermodynamically Driven Reversible Infuser Pump for Use as a Remotely Controlled Gastric Band," issued Apr. 1, 2008, the disclosure of which is incorporated by reference herein. Of course, any other suitable type of pump may be used. Another variation of gastric band system (10) may include a hydrogel actuated switch mechanism (not shown) in communication with such a pump (not shown).

For instance, such a switch mechanism may include a housing in which a hydrogel resides, with the housing being located within the stomach (2), and with the housing including pores or openings permitting fluid inside the stomach (2) to contact the hydrogel. The housing may also include a switch that is closed by swelled hydrogel; and that is left open when the hydrogel is collapsed. Such a switch may include a conventional or custom electromechanical switch that is resiliently biased to an open position. The hydrogel may swell in response to a relatively high pH level as described above with respect to hydrogel (122). When the switch is closed by swelled hydrogel (e.g., when the patient begins eating), such closing of the switch may activate the pump to drive more fluid into bladder (22), to place gastric band (20) in the configuration shown in FIG. 4. When the switch is opened by collapsed hydrogel (e.g., when the patient is fasting or otherwise not eating), such opening of the switch may activate the pump to draw fluid from bladder (22), to place gastric band (20) in the configuration shown in FIG. 3. The switch mechanism may be in communication with the pump via a wire fed through stomach wall (3). Alternatively, the switch mechanism may be in communication with the pump wirelessly.

As yet another merely illustrative variation, a hydrogel based switch mechanism may be coupled with a gastric valve to activate driving of the valve between substantially restrictive and substantially non-restrictive configurations. For instance, a hydrogel based switch mechanism may be coupled with a gastric valve as described in U.S. Pub. No. 2006/0235448, entitled "Artificial Gastric Valve," published Oct. 19, 2006, the disclosure of which is incorporated by reference herein. Various suitable ways in which a hydrogel based switch mechanism may be coupled with such a gastric valve will be apparent to those of ordinary skill in the art in view of the teachings herein. Various other suitable components, features, and configurations, and uses for such a hydrogel based switch mechanism will also be apparent to those of ordinary skill in the art in view of the teachings herein.

Hydrogel Actuated Space Occupying Device

Figure 8A:
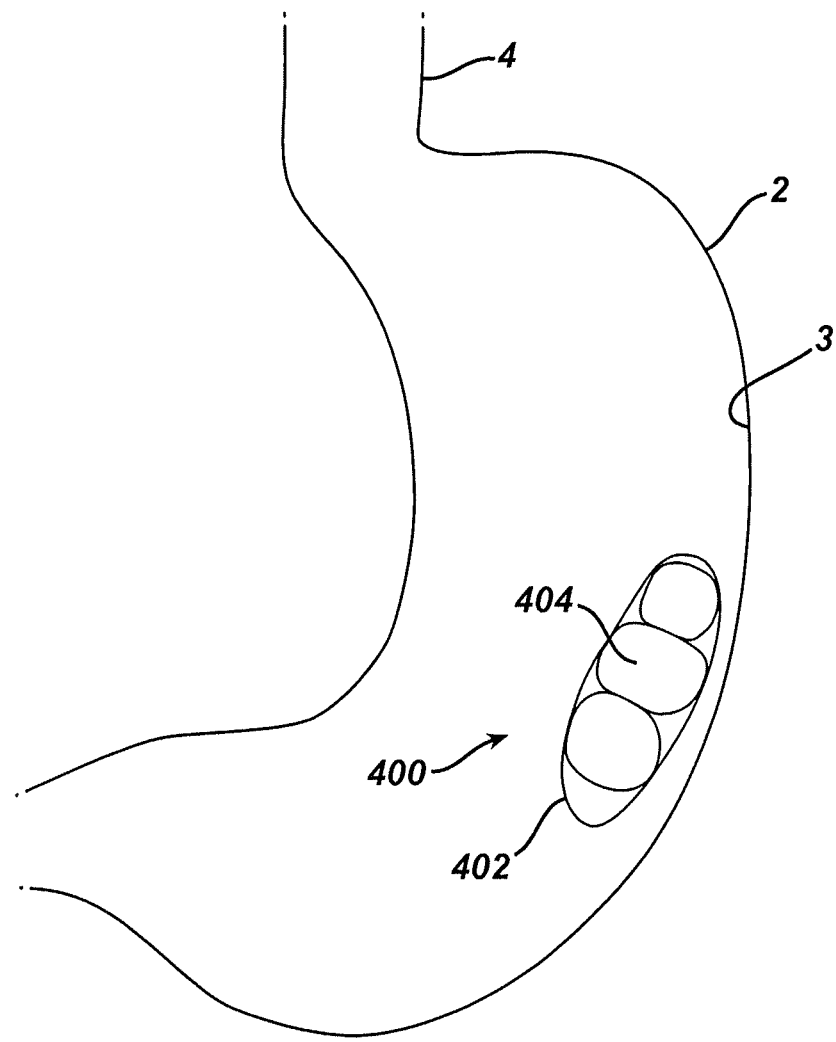
FIG. 8A depicts a schematic view of an exemplary hydrogel space occupying device, with the hydrogel in a collapsed state.
Figure 8B:
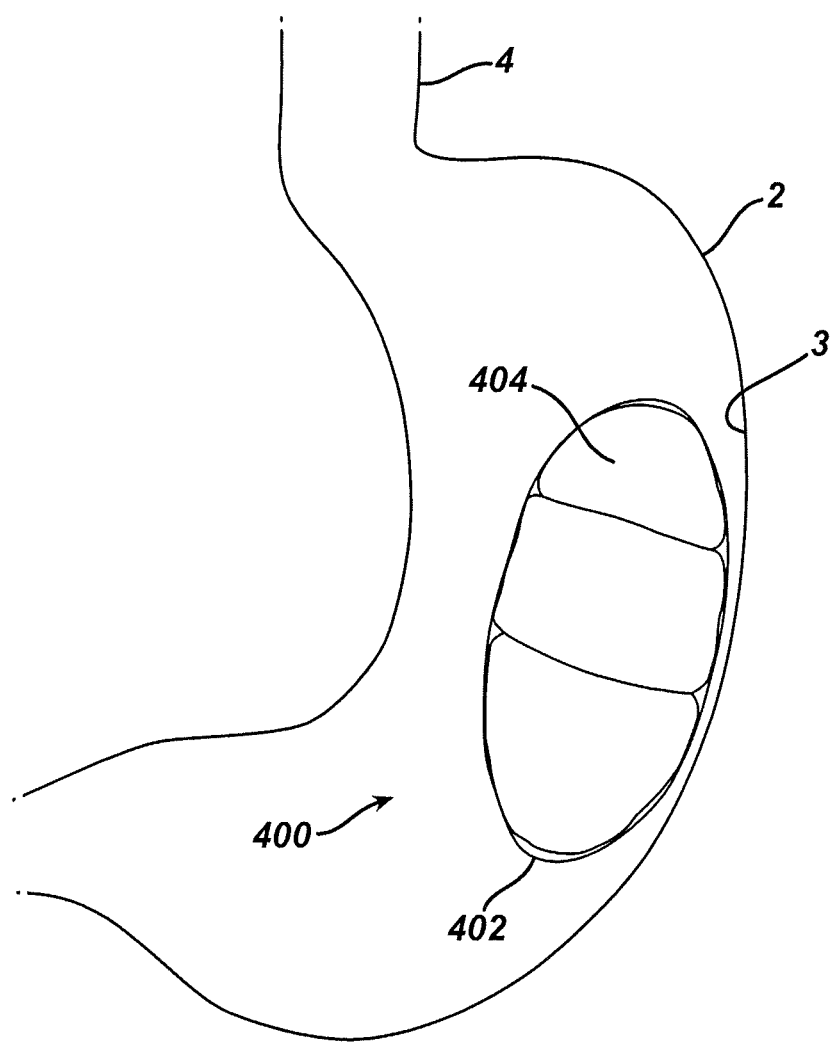
FIG. 8B depicts a schematic view of the hydrogel space occupying device of FIG. 8A, with the hydrogel in an expanded state.

FIGS. 8A-8B illustrate an exemplary hydrogel space occupying device (400) that may be provided within a patient's stomach (2). Space occupying device (400) of this example comprises a pouch or jacket (402) housing a plurality of hydrogel pellets (404). While three hydrogel pellets (404) are shown, it should be understood that any other suitable number of hydrogel pellets (404) may be used, including but not limited to just one single hydrogel pellet (404). Jacket (402) may be secured within a patient's stomach (2) (e.g. to the wall (3) of stomach (2)) using sutures, staples, tacks, rivets adhesives, and/or using any other suitable components, devices, or techniques, including combinations thereof.

Jacket (402) of the present example is formed of a porous, extensible material that can substantially withstand acid and other fluids in the stomach (2), grinding and churning mechanisms of gastric motility, and enzymatic attack by digestive enzymes. The porous property of jacket (402) permits fluid in stomach (2) to contact hydrogel pellets (404), such that gastric fluids may enter and leave jacket (402) freely to allow changing physiological conditions occurring in stomach (2) (e.g., relating to consumption and fasting) to also occur inside jacket (402). Jacket (402) may have openings formed in it in addition to or as an alternative to being formed of a porous material. The extensible property of jacket (402) permits jacket (402) to expand with hydrogel pellets (404) when hydrogel pellets (404) swell as described in greater detail below. In some other versions, jacket (402) is flexible but non-extensible. For instance, jacket (402) may non-extensibly collapse with hydrogel pellets (404) in the configuration shown in FIG. 8A; and may non-extensibly flex to accommodate swelled hydrogel pellets (404) in the configuration shown in FIG. 8B. By way of example only, jacket (402) may be formed of any of the following materials, including combinations thereof: metals such as NiTi; polyesters such as polyethylene terephthalate or PET; polyolefins such as polypropylene, polyethylene, and copolymers; silicone elastomers from the family of polymers based on dimethyl siloxane, including materials functionalized with phenyl or fluro groups to include phenyl silicones and fluorosilicones; fluoropolymers such as expanded PTFE, PTFE, copolymers or terpolymers synthesized with monomer groups containing tetrafluoroetheylene (TFE), hexafluoropropylene (HFP), vinylidene fluoride (VDF), and others that make up the class of materials known as fluoropolymers and fluoroelastomers. Other suitable materials and combinations of materials will be apparent to those of ordinary skill in the art in view of the teachings herein. Similarly, other various alternative ways in which space occupying device (400) may be configured, including but not limited to other components that may be provided on or within jacket (402), will be apparent to those of ordinary skill in the art in view of the teachings herein.

The hydrogel that forms hydrogel pellets (404) in the present example is environmentally sensitive, such that hydrogel pellets (404) will change between a collapsed state (FIG. 8A) and a swelled state (FIG. 8B). In particular, the hydrogel of hydrogel pellets (404) is formulated and configured such that it is in a collapsed state in a low pH environment (FIG. 8A); and such that it will swell in response to an increased pH level (FIG. 8B). Those of ordinary skill in the art will recognize that an increase in pH may be caused when the patient begins to consume food, and that the pH level in the stomach (2) may go down when the patient is fasting or otherwise not consuming food. By way of example only, hydrogel pellets (404) may be formulated and configured such that they swell to an expanded state (FIG. 8B) when they are exposed to a pH level that is at or greater than approximately 4 (or at or greater than approximately 5); and such that they shrink to a collapsed state (FIG. 8A) when they are exposed to a pH level that is less than approximately 4 (or less than approximately 5). Alternatively, hydrogel pellets (404) may be formulated and configured such that they swell or shrink in response to any other suitable pH levels.

In view of the foregoing, it should be understood that before a patient begins consuming food, hydrogel pellets (404) may be in the collapsed state shown in FIG. 8A. At this time, space occupying device (400) occupies a relatively minimal amount of volume within the patient's stomach (2), such that space occupying device (400) has a relatively negligible effect on the patient's satiety. As the patient begins to consume food, the pH level in the patient's stomach (2) begins to rise. This increase in pH is sensed by hydrogel pellets (404) due to fluid in stomach (2) communicating with hydrogel pellets (404) via jacket (402). In response to this increase in pH, hydrogel pellets (404) swell to the expanded state shown in FIG. 8B. This swelling of hydrogel pellets (404) reduces the capacity of empty volume in the patient's stomach (2), thereby providing a relatively early sense of satiety in the patient upon or shortly after the patient begins consuming food. The patient may then cease their food intake earlier than they otherwise would in the absence of space occupying device (400). After the patient is done eating, the patient's physiology eventually returns to the fasting stage, and the pH level in the patient's stomach decreases. This decrease in pH level causes hydrogel pellets (404) to shrink back to the collapsed configuration shown in FIG. 8A. Of course, a variety of features and components of space occupying device (400) may be modified, substituted, or supplemented in various ways; if not be omitted altogether. Numerous suitable variations of space occupying device (400) will be apparent to those of ordinary skill in the art in view of the teachings herein. By way of example only, some versions may include two or more space occupying devices (400) being positioned at different locations within the patient's stomach (2).

Hydrogel Actuated Gastric Sleeve

Figure 9A:
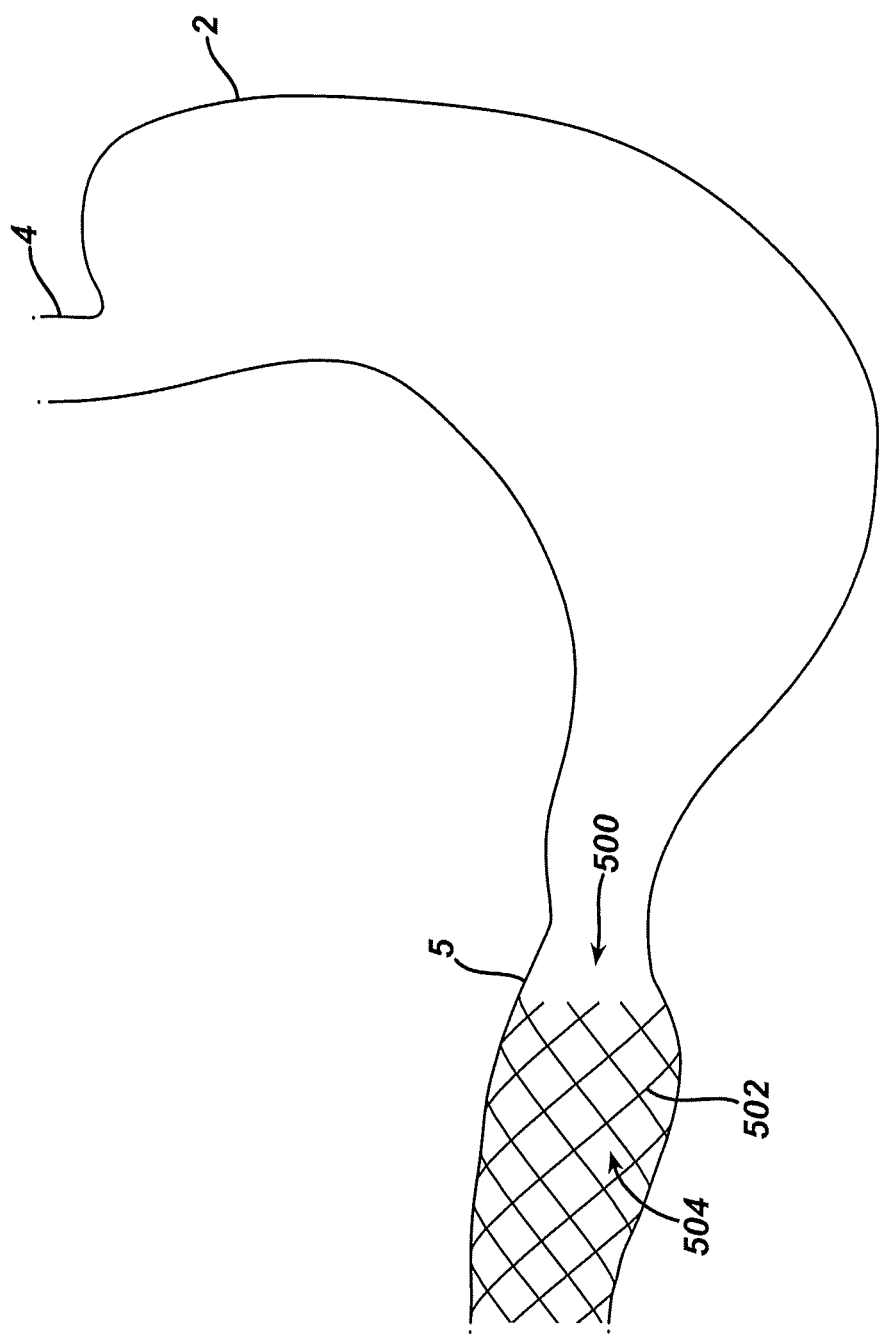
FIG. 9A depicts a schematic view of an exemplary hydrogel actuated gastric sleeve, with the hydrogel in a collapsed state.
Figure 9B:
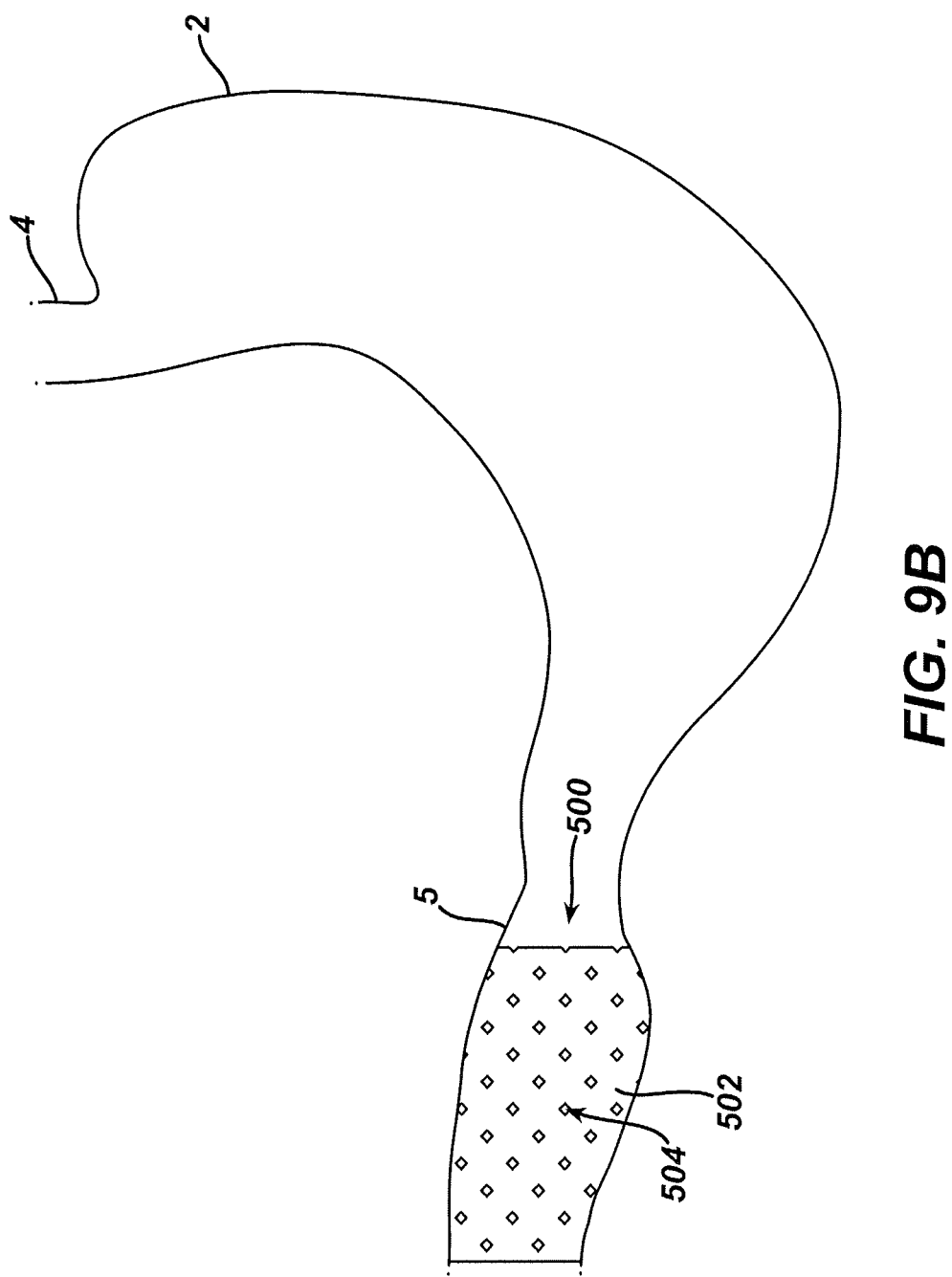
FIG. 9B depicts a schematic view of the hydrogel actuated gastric sleeve of FIG. 9A, with the hydrogel in an expanded state.

FIGS. 9A-9B illustrate an exemplary hydrogel actuated gastric sleeve (500). Gastric sleeve (500) is installed in the patient's duodenum (5) in the present example, though it should be understood that gastric sleeve (500) may alternatively be positioned at any other suitable location within the patient's gastrointestinal tract (e.g., within stomach (5) and/or esophagus (4), etc.). Gastric sleeve (500) of this example comprises a hydrogel impregnated body (502) that forms a mesh-like construction defining a plurality of openings (504). Hydrogel impregnated body (502) is substantially cylindraceous and elongate, such that it may be installed directly against the inner surface of the duodenum (5). By way of example only, hydrogel impregnated body (502) may be fixed in place within the duodenum (5) using sutures, staples, tacks, rivets adhesives, and/or using any other suitable components, devices, or techniques, including combinations thereof. In the present example, hydrogel impregnated body (502) has a substantially hollow interior along its longitudinal axis, such that food and fluids may be communicated longitudinally through hydrogel impregnated body (502). In addition, hydrogel impregnated body (502) remains fixed within the duodenum (5), regardless of whether hydrogel impregnated body (502) is in a collapsed state (FIG. 9A) or a swelled state (FIG. 9B).

Hydrogel impregnated body (502) is environmentally sensitive, such that the hydrogel will change between a collapsed state (FIG. 9A) and a swelled state (FIG. 9B). In particular, the hydrogel impregnating the body (502) is formulated and configured such that it is in a collapsed state in a low pH environment (FIG. 9A); and such that it will swell in response to an increased pH level (FIG. 9B). Those of ordinary skill in the art will recognize that an increase in pH may be caused when the patient begins to consume food, and that the pH level in the stomach (2) may go down when the patient is fasting or otherwise not consuming food. By way of example only, the hydrogel impregnating the body (502) may be formulated and configured such that it swells to an expanded state (FIG. 9B) when it is exposed to a pH level that is at or greater than approximately 4 (or at or greater than approximately 5); and such that it shrinks to a collapsed state (FIG. 9A) when it is exposed to a pH level that is less than approximately 4 (or less than approximately 5). Alternatively, the hydrogel impregnating the body (502) may be formulated and configured such that it swells or shrinks in response to any other suitable pH levels.

Hydrogel may be impregnated into body (502) using a process similar to known processes of impregnating vascular grafts with collagen; or using any other suitable process or combination of processes. For instance, they hydrogel polymer may essentially be formed (synthesized) in situ, directly on body (502). Such synthesis may be a liquid reaction, such that the liquid impregnates the porous body (502), forming an interpenetrating network. Various other suitable ways in which hydrogel may be impregnated into body (502), and/or other suitable ways in which hydrogel may otherwise be incorporated into body (502), will be apparent to those of ordinary skill in the art in view of the teachings herein.

When hydrogel impregnated body (502) is in the collapsed state as shown in FIG. 9A, its matrix or mesh like configuration defines relatively large openings (504). These relatively large openings (504) permit substantially free communication of nutrients to the inner surface of the duodenum (5), where nutrients are absorbed through the inner surface. When hydrogel impregnated body (502) swells to the expanded state shown in FIG. 9B, openings (504) shrink in size. These relatively small openings (504) substantially restrict communication of nutrients to the inner surface of the duodenum (5). In some versions, openings (504) may be reduced in size so much that they prevent communication of nutrients to the inner surface of duodenum (5) along the full length of hydrogel impregnated body (502). Such restriction or prevention of communication of nutrients to the inner surface of duodenum (5) may substantially restrict or prevent the duodenum (5) from absorbing such nutrients. In some settings, such prevention of nutrient absorption may result in weight loss in the patient, as described in U.S. Pub. No. 2008/0269715, entitled "Use of an Adhesive as an Intestinal Barrier for Bariatrics," published Oct. 30, 2008, the disclosure of which is incorporated by reference herein.

In view of the foregoing, it should be understood that before a patient begins consuming food, gastric sleeve (500) may be in the collapsed state shown in FIG. 9A. At this time, openings (504) are relatively large. As the patient begins to consume food, the pH level in the patient's duodenum (5) begins to rise. This increase in pH is sensed by hydrogel impregnated body (502) due to fluid in duodenum (5) communicating with hydrogel impregnated body (502). In response to this increase in pH, gastric sleeve (500) swells to the expanded state shown in FIG. 9B. This swelling significantly reduces the size of openings (504), thereby restricting or preventing the absorption of nutrients through duodenum (5) from food communicated through gastric sleeve (500). After the patient is done eating, the patient's physiology eventually returns to the fasting stage, and the pH level in the patient's duodenum (5) decreases. This decrease in pH level causes hydrogel gastric sleeve (500) to shrink back to the collapsed configuration shown in FIG. 9A, which in turn increases the size of openings (504). Of course, a variety of features and components of gastric sleeve (500) may be modified, substituted, or supplemented in various ways; if not be omitted altogether. Numerous suitable variations of gastric sleeve (500) will be apparent to those of ordinary skill in the art in view of the teachings herein.

In a merely illustrative variation of gastric sleeve (500), gastric sleeve (500) is installed in the patient's esophagus (4), just above the stomach (2) (e.g., just above the lower esophageal sphincter), and the responsiveness of hydrogel impregnated body (502) to pH levels is reversed. In particular, hydrogel impregnated body (502) is configured to swell in response to a low pH level (FIG. 9B) and collapse in response to a high pH level (FIG. 9A). Such a reversed response may be suitable in a scenario where gastric sleeve (500) is being used to treat gastroesophageal reflux disease (GERD) or some other condition (e.g., rather than being used to treat morbid obesity). That is, stomach acid that is refluxed into esophagus (4) may cause hydrogel impregnated body (502) to swell, which may significantly reduce the size of openings (504), which may in turn allow gastric sleeve (500) to essentially act as a shield for tissue of the esophagus (4) against the refluxed acid. Thus, swelling hyrdogel impregnated body (502) in response to an occurrence of undesired acid reflux may reduce the likelihood of harm caused to esophagus (4) by such acid reflux. Still other suitable ways in which a gastric sleeve (500) (or variations thereof) may be used will be apparent to those of ordinary skill in the art in view of the teachings herein.

Consumption Tracking Using Hydrogel

As another merely illustrative example, an environmentally sensitive hydrogel may be used formulated and configured such that it is sensitive to glucose concentrations. By way of example only, changes in glucose concentration can be used to monitor food intake, track patterns, and potentially provide a signal for a change in eating habits, band adjustment, physician visit, etc. In addition or in the alternative, nutritional intake information may be compared to physical activity via heart rate monitoring and/or other physiological parameters. In addition or in the alternative, nutritional intake information may be used to create an algorithm balancing energy in vs. energy out. Such an algorithm may be used to trigger or signal a restriction by a gastric band (20), adjustment a gastric band (20), signal information to patient or physician that behavior modification or adjustment is required, etc. Various other suitable ways in which nutritional intake information may be used will be apparent to those of ordinary skill in the art in view of the teachings herein.

Miscellaneous

While most of the examples described herein relate to the treatment of morbid obesity, it should be understood that the teachings herein may also be applied to the treatment of a variety of other conditions, including but not limited to acid reflux, incontinence (e.g., urinary incontinence, fecal incontinence), motility disorders (e.g., gastroparesis, dumping syndrome, etc.), and/or other conditions, including combinations of conditions. Various ways in which the teachings herein may be used to treat such other conditions, in addition to or in lieu of treating morbid obesity, will be apparent to those of ordinary skill in the art.

It will also become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Versions of the present invention have application in conventional endoscopic and open surgical instrumentation as well as application in robotic-assisted surgery.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a sensor device configured for implantation within a patient's gastrointestinal tract, wherein the sensor device comprises:
      (i) a hydrogel that senses a physiological parameter associated with consumption of food by the patient, wherein the hydrogel swells or collapses in response to sensing a physiological parameter associated with consumption of food by the patient, and
      (ii) a fluid reservoir containing an actuation fluid, wherein the fluid reservoir is defined by the hydrogel;
   (b) a restriction forming device configured for implantation within the patient, wherein the restriction forming device is configured to form a restriction in an anatomical structure of the patient, wherein the restriction forming device is coupled with the sensor device via a conduit such that the restriction forming device and the sensor device are in fluid communication via the conduit, wherein the restriction forming device selectively varies the degree of restriction formed by the restriction forming device based at least in part on whether the hydrogel is in a swelled state or a collapsed state, wherein the restriction forming device contains a fluid, wherein the degree of restriction formed by the restriction forming device is based on an amount of fluid in the restriction forming device, wherein the hydrogel is formulated to swell in response to being exposed to gastric fluids indicating consumption of food by the patient such that swelling by the hydrogel forces actuation fluid from the reservoir toward the restriction forming device to add fluid to the restriction forming device to thereby increase the degree of restriction formed by the restriction forming device; and
   (c) a catheter, wherein the catheter couples the restriction forming device with the fluid reservoir of the sensor device such that the fluid reservoir of the sensor device is in communication with the restriction forming device.

2. The apparatus of claim 1, wherein the restriction forming device comprises a gastric band.

3. The apparatus of claim 2, wherein the gastric band comprises a bladder, wherein the size of the restriction formed by the gastric band is based on an amount of fluid in the bladder, wherein the amount of fluid in the bladder is based at least in part on whether the hydrogel is in the swelled state or the collapsed state.

4. The apparatus of claim 1, wherein the sensor device comprises a housing having a first section and a second section, wherein the fluid reservoir is defined in the first section of the housing, wherein the second section of the housing contains the hydrogel, wherein the second section of the housing defines a plurality of openings that permit communication of gastric fluids through the housing to reach the hydrogel.

5. The apparatus of claim 4, wherein the sensor device further comprises a piston disc in the housing, wherein the piston disc is positioned between the hydrogel and the actuation fluid, such that the piston disc provides a movable barrier separating the first section of the housing from the second section of the housing.

6. The apparatus of claim 4, wherein the hydrogel is formulated to swell in response to being exposed to gastric fluids indicating consumption of food by the patient such that swelling by the hydrogel forces actuation fluid from the first section of the housing toward the restriction forming device to add fluid to the restriction forming device to thereby increase the degree of restriction formed by the restriction forming device.

7. The apparatus of claim 1, further comprising a jacket external to the hydrogel, wherein the jacket permits communication of gastric fluids through the jacket to reach the hydrogel.

8. The apparatus of claim 7, wherein the jacket is non-extensible, such that the jacket substantially prevents outward swelling of the hydrogel, thereby forcing inward swelling of the hydrogel.

9. The apparatus of claim 1, wherein the hydrogel has a substantially hollow spherical shape.

10. The apparatus of claim 1, wherein the restriction forming device comprises a gastric sleeve.

11. The apparatus of claim 10, wherein the gastric sleeve comprises a body, wherein the body is formed of a material impregnated by the hydrogel.

12. The apparatus of claim 11, wherein the body comprises a plurality of openings, wherein the size of the openings is based on whether the hydrogel impregnating the body is in the swelled state or the collapsed state, wherein the size of the openings is reduced when the hydrogel impregnating the body is in the swelled state, wherein the reduced size openings restricts absorption of nutrients by the anatomical structure of the patient.

13. The apparatus of claim 1, wherein the hydrogel is responsive to pH levels associated with consumption of food by the patient, such that the hydrogel is in the swelled state or the collapsed state based on a pH level within the patient.

14. An apparatus, comprising:
   (a) a sensor device configured for implantation within a patient's gastrointestinal tract, wherein the sensor device comprises:
      (i) a hydrogel that senses a physiological parameter associated with consumption of food by the patient, wherein the hydrogel swells or collapses in response to sensing a physiological parameter associated with consumption of food by the patient, and
      (ii) a fluid reservoir containing an actuation fluid, wherein the fluid reservoir is defined by the hydrogel;
   (b) a restriction forming device configured for implantation within the patient, wherein the restriction forming device is configured to form a restriction in an anatomical structure of the patient, wherein the restriction forming device is coupled with the sensor device via a conduit such that the restriction forming device and the sensor device are in fluid communication via the conduit, wherein the restriction forming device selectively varies the degree of restriction formed by the restriction forming device based at least in part on whether the hydrogel is in a swelled state or a collapsed state, wherein the restriction forming device contains a fluid, wherein the degree of restriction formed by the restriction forming device is based on an amount of fluid in the restriction forming device, wherein the hydrogel reservoir is formulated to collapse in response to being exposed to gastric fluids indicating consumption of food by the patient such that collapsing by the hydrogel reservoir forces actuation fluid from the reservoir toward the restriction forming device to add fluid to the restriction forming device to thereby increase the degree of restriction formed by the restriction forming device; and (c) a catheter, wherein the catheter couples the restriction forming device with the fluid reservoir of the sensor device such that the fluid reservoir of the sensor device is in communication with the restriction forming device.

\* \* \* \* \*